(12) United States Patent
Burgoon et al.

(10) Patent No.: US 9,938,241 B2
(45) Date of Patent: Apr. 10, 2018

(54) DIAZIRINE COMPOUNDS AND COMPOSITIONS DERIVED THEREFROM

(71) Applicant: PROMERUS, LLC, Brecksville, OH (US)

(72) Inventors: Hugh Burgoon, Brecksville, OH (US); Crystal D. Cyrus, Brecksville, OH (US); Larry F. Rhodes, Brecksville, OH (US)

(73) Assignee: PROMERUS, LLC, Brecksville, OH (US)

( * ) Notice: Subject to any disclaimer, the term of this patent is extended or adjusted under 35 U.S.C. 154(b) by 145 days.

(21) Appl. No.: 14/862,418

(22) Filed: Sep. 23, 2015

(65) Prior Publication Data

US 2016/0083352 A1    Mar. 24, 2016

Related U.S. Application Data

(60) Provisional application No. 62/053,921, filed on Sep. 23, 2014.

(51) Int. Cl.
| | | |
|---|---|---|
| *C07D 229/02* | (2006.01) | |
| *G03F 7/004* | (2006.01) | |
| *G03F 7/40* | (2006.01) | |
| *C07D 403/14* | (2006.01) | |
| *C07D 401/14* | (2006.01) | |
| *C08K 5/3442* | (2006.01) | |

(52) U.S. Cl.
CPC ......... *C07D 229/02* (2013.01); *C07D 401/14* (2013.01); *C07D 403/14* (2013.01); *C08K 5/3442* (2013.01); *G03F 7/0045* (2013.01); *G03F 7/40* (2013.01); *C08F 2810/20* (2013.01); *C08G 2261/135* (2013.01); *C08G 2261/143* (2013.01); *C08G 2261/144* (2013.01); *C08G 2261/146* (2013.01); *C08G 2261/1412* (2013.01); *C08G 2261/1414* (2013.01); *C08G 2261/1422* (2013.01); *C08G 2261/1424* (2013.01); *C08G 2261/3324* (2013.01); *C08G 2261/418* (2013.01); *C08G 2261/76* (2013.01)

(58) Field of Classification Search
CPC ...... G03F 7/0045; G03F 7/038; G03F 7/0758; C07D 229/02
USPC ................. 430/270.1, 919, 920; 548/960
See application file for complete search history.

(56) References Cited

U.S. PATENT DOCUMENTS

| | | | | | |
|---|---|---|---|---|---|
| 4,571,375 | A | * | 2/1986 | Benedikt | G03F 7/0125 430/194 |
| 6,156,478 | A | * | 12/2000 | Liu | G03F 7/0125 428/304.4 |
| 2012/0322978 | A1 | * | 12/2012 | Huang | C07D 229/02 530/330 |
| 2015/0017246 | A1 | * | 1/2015 | Huang | C07K 17/10 424/490 |
| 2016/0159777 | A1 | * | 6/2016 | Huang | C07D 229/02 530/300 |

FOREIGN PATENT DOCUMENTS

WO    WO 2005/056582 A1    6/2005
WO    WO 2013/012961 A2    1/2013

OTHER PUBLICATIONS

Welle, Alexandre; Billard, Francois; Marchand-Brynaert, Jacqueline; Tri-and tetravealent Photoactivable cross-linking agents, Synthesis (2012) ; 44(14): pp. 2249-2254.*
Kristi Simonton et al., "Novel Photocrosslinking Molecules," RadTech e/5, 2006, Technical Proceedings, 2006, 10 pages.
Hakim Mehenni et al., "Synthesis and Application of New Photocrosslinkers for Poly(ethylene glycol)," Australian Journal of Chemistry, vol. 65, No. 2, 2012, pp. 193-201.
Alexandre Welle et al., "Tri- and Tetravalent Photoactivable Cross-Linking Agents," Synthesis, vol. 44, No. 14, 2012, pp. 2249-2254.
Svenja Bockelmann et al., "Archazolid A Binds to the Equatorial Region of the c-Ring of the Vacuolar H+-ATPase," Journal of Biological Chemistry, vol. 285, No. 49, 2010, pp. 38304-38314.
Fabia Hentschel et al., "Synthesis and Cytotoxicity of a Diazirine-Based Photopsammaplin," Europena Journal of Organic Chemistry, 2014, pp. 2120-2127.

* cited by examiner

*Primary Examiner* — John S Chu
(74) *Attorney, Agent, or Firm* — Balaram Gupta

(57) ABSTRACT

A series of diazirine compounds of formula (I) having utility as photocrosslinkers are disclosed.

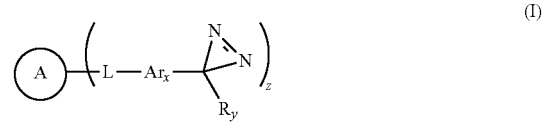

(I)

Where, A, L, z, $Ar_x$ and $R_y$ are as defined herein. Also disclosed are the photodefinable compositions containing these compounds.

17 Claims, 2 Drawing Sheets

DIAZIRINE COMPOUNDS AND COMPOSITIONS DERIVED THEREFROM

CROSS REFERENCE TO RELATED APPLICATIONS

This application claims the benefit of U.S. Provisional Application No. 62/053,921, filed Sep. 23, 2014, which is incorporated herein by reference in its entirety.

BACKGROUND OF THE INVENTION

Field of the Invention

The present invention relates to a series of diazirine compounds. More specifically, the present invention relates to a series of bis-diazirines, tris-diazirines and tetrakis-diazirines, and the like, having utility as photocrosslinkers. This invention also relates to photodefinable compositions containing these diazirine compounds.

Description of the Art

There has been a growing interest in developing new electronic materials featuring superior chemical, optical and mechanical properties, which are environmentally friendly and can be processed under aqueous conditions. Most notably, there is a growing demand for developing materials which are capable of forming micron-level structures. In particular, micron-level device geometries have become common place in the fabrication of a variety of liquid crystal displays (LCDs), organic light emitting diodes (OLEDs) and other radio frequency (RF) and microwave devices. For example, devices such as radio frequency integrated circuits (RFICs), micro-machine integrated circuits (MMICs), switches, couplers, phase shifters, surface acoustic wave (SAW) filters and SAW duplexers, have recently been fabricated in the micron-levels.

In addition, there has been growing interest in organic electronic (OE) devices, for example, organic field effect transistors (OFET) for use in backplanes of display devices or logic capable circuits, and organic photovoltaic (OPV) devices, among others. A conventional OFET has a gate electrode, a gate insulator layer made of a dielectric material (also referred to as "dielectric" or "gate dielectric"), source and drain electrodes, a semiconducting layer made of an organic semiconductor (OSC) material, and typically a passivation layer on top of the aforementioned layers to provide protection against environmental influence or against damage from subsequent device manufacturing steps.

In most electronic and optoelectronic devices, the OSC material employed must feature certain requisite properties including low permittivity ("low-k"), non-charge trapping, and orthogonality to other organic materials used therewith. In addition, there is also a need for good cross-linking functionality which often is difficult to incorporate without modifying the low permittivity. The current materials also employ a variety of fluorinated solvents which are not only environmentally unfriendly but also not cost effective.

Accordingly, it is an object of this invention to provide a series of bis-diazirines, tris-diazirines and tetrakis-diazirines, and the like, which are found to be effective photocrosslinkers.

It is also an object of this invention to provide a variety of photoimageable compositions, which can be used in a variety of applications including in the fabrication of electronic, optoelectronic devices.

Other objects and further scope of the applicability of the present invention will become apparent from the detailed description that follows.

SUMMARY OF THE INVENTION

Surprisingly, it has now been found that certain of the bis-diazirines, tris-diazirines or tetrakis-diazirines, when suitably exposed to radiation releases dinitrogen forming a reactive carbene intermediate, which aspect can be exploited to make photoimageable compositions. The highly active carbene thus formed in situ can insert (i.e., react) into one or more other materials either via inserting into an OH, NH, CH or olefin functionality of such materials or other functionality that may be present to form the cross-linked insertion product. Thus, a compound having two or more diazirine functionalities (i.e., bis- or tris-diazirines, etc.) would have the ability to crosslink one or more materials, such as the polymeric materials used in the fabrication of electronic or optoelectronic devices as described herein. It has been reported that certain compounds which can generate nitrene intermediates can be used in the fabrication of such electronic and/or optoelectronic devices. Thus, it is envisioned that the compounds of this invention are more suitable for such application as they may feature even lower permittivity properties (lower k due to no heteroatom) than the corresponding nitrene generating compounds but also may provide higher cross-linking capability as a carbene is expected to be more reactive than a nitrene. It is further expected that the nitrene inserted product results in an amine which can be a source for charge trapping, whereas carbene inserted product produces no such product. It should further be noted that the commonly known carbene precursors such as certain diazo compounds are unstable, however, the bis-(diazirines), tris-(diazirines) and tetrakis-(diazirines) as disclosed herein are stable compounds.

Accordingly, there is provided a compound of the formula (I):

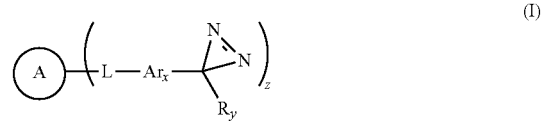

Wherein, A is a carbon, silicon, oxygen or nitrogen central core moiety;

L is a bond or a divalent linking or a spacer group selected from ether, ketone, amine, sulfide, sulfone, ester, amide or a combination thereof; $Ar_x$ is an aromatic or heteroaromatic group and $R_y$ is an alkyl, aryl, arylalkyl, partly fluorinated or perfluorinated alkyl, aryl and arylalkyl group; and z is an integer from 2 to 4. Non-limiting examples of central core moiety A can be selected from aliphatic, cycloaliphatic, heteroaliphatic, heterocycloaliphatic, aromatic or heteroaromatic moieties.

In another aspect there is provided a compound of formula (IA):

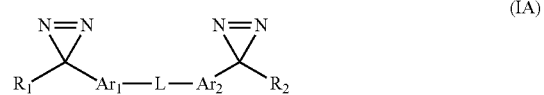

Wherein,

L is a bond or a divalent linking or a spacer group selected from:

—C(O)O—R$_4$—OC(O)—, —C(O)O—R$_4$—, —R$_4$—OC(O)—R$_4$—, —C(O)—R$_4$—OC(O)—, —C(O)—R$_4$—, —R$_4$—C(O)—R$_4$—, —O—R$_4$—OC(O)—, —O—R$_4$—O—, —O—R$_4$—, —R$_4$—O—R$_4$—, —C(O)NR$_5$—R$_4$—OC(O)—, —C(O)NR$_5$—R$_4$—NR$_5$C(O)—, —C(O)NR$_5$—R$_4$—, —R$_4$—NR$_5$C(O)—R$_4$—, —C(O)—R$_4$—NR$_5$C(O)—, —NR$_5$—R$_4$—OC(O)—, —NR$_5$—R$_4$—NR$_5$C(O)—, —NR$_5$—R$_4$—, —R$_4$—NR$_5$—R$_4$—, —NR$_5$—R$_4$—NR$_5$—

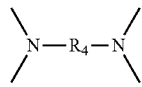

and —R$_4$—, where each occurrence of R$_4$ may be the same or different which is a divalent group independently selected from (C$_1$-C$_{12}$)alkyl, (C$_3$-C$_{12}$)cycloalkyl, (C$_6$-C$_{12}$)aryl, (C$_6$-C$_{12}$)aryl(C$_1$-C$_{12}$)alkyl, (C$_6$-C$_{10}$)heteroaryl, (C$_6$-C$_{10}$)heteroaryl(C$_1$-C$_{12}$)alkyl, —(CH$_2$—CH$_2$—O)$_a$—, where a is an integer from 1 to 10, provided that when R$_4$ is —(CH$_2$—CH$_2$—O)$_a$— then the oxygen end of said group is linked only with either carbon or silicon containing linking group, which are optionally substituted with a group selected from halogen, —OH, (C$_1$-C$_4$)alkyl, (C$_1$-C$_4$)alkoxy, (C$_6$-C$_{10}$)aryl, (C$_6$-C$_{10}$)aryloxy, (C$_6$-C$_{12}$)aralkyl and (C$_6$-C$_{12}$)aralkyloxy; and R$_5$ is hydrogen, (C$_1$-C$_6$)alkyl, (C$_6$-C$_{10}$)aryl or (C$_6$-C$_{10}$) aralkyl;

R$_1$ and R$_2$ are the same or different and each is independently selected from (C$_1$-C$_{12}$)alkyl, where portions of hydrogen on alkyl are replaced with fluorine, (C$_1$-C$_{12}$) perfluoroalkyl, (C$_6$-C$_{12}$)aryl, (C$_6$-C$_{12}$)aryl(C$_1$-C$_{12}$)alkyl, where portions of hydrogen on alkyl are replaced with fluorine, and (C$_6$-C$_{12}$)arylperfluoro(C$_1$-C$_{12}$)alkyl; and Ar$_1$ and Ar$_2$ are the same or different and each is independently selected from (C$_6$-C$_{12}$)arylene or (C$_6$-C$_{12}$)heteroarylene group optionally substituted with a group selected from halogen, —OH, (C$_1$-C$_4$)alkyl, (C$_1$-C$_4$)alkoxy, (C$_6$-C$_{10}$)aryl, (C$_6$-C$_{12}$)aryloxy, (C$_6$-C$_{12}$)aryl(C$_1$-C$_4$)alkyl and (C$_6$-C$_{12}$)aryl(C$_1$-C$_4$)alkyloxy; and with the proviso that the following compounds are excluded:

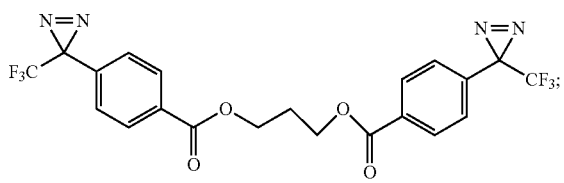

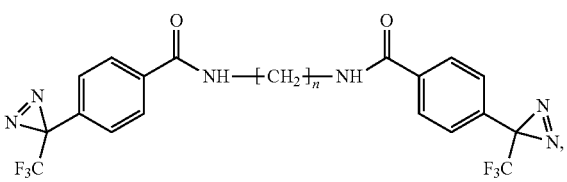

where n is 7 or 12; and

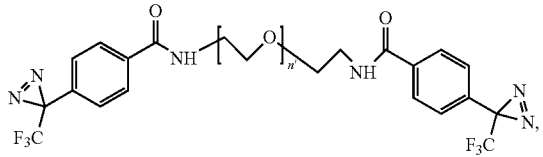

where n' is 3 or 5.

In another aspect of this invention there is also provided a compound of formula (II) or (IIA):

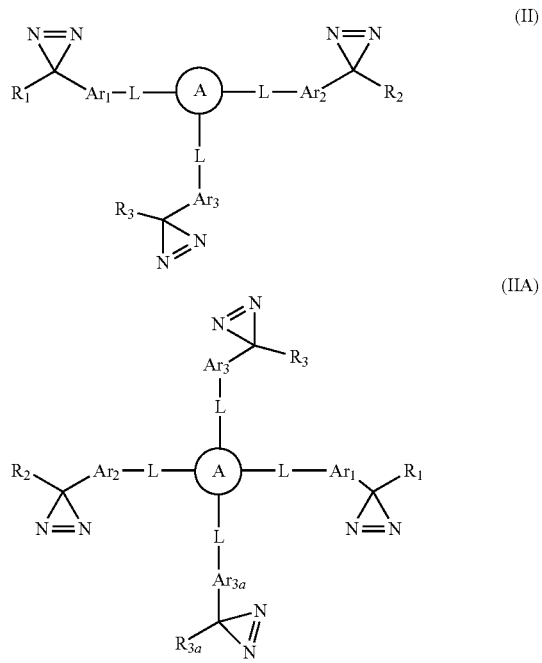

Where L, A, Ar$_1$, Ar$_2$, R$_1$ and R$_2$ are as defined herein. Ar$_3$ and Ar$_{3a}$ may be the same as Ar$_1$ and Ar$_2$ and are independently of each other selected from (C$_6$-C$_{12}$)arylene or (C$_6$-C$_{12}$)heteroarylene group optionally substituted with a group selected from halogen, —OH, (C$_1$-C$_4$)alkyl, (C$_1$-C$_4$)alkoxy, (C$_6$-C$_{10}$)aryl, (C$_6$-C$_{12}$)aryloxy, (C$_6$-C$_{12}$)aryl(C$_1$-C$_4$)alkyl and (C$_6$-C$_{12}$)aryl(C$_1$-C$_4$)alkyloxy. Similarly, R$_3$ and R$_{3a}$ may be the same as R$_1$ and R$_2$ and are independently of each other selected from (C$_1$-C$_{12}$)alkyl, where portions of hydrogen on alkyl are replaced with fluorine, (C$_1$-C$_{12}$)perfluoroalkyl, (C$_6$-C$_{12}$)aryl, (C$_6$-C$_{12}$)aryl(C$_1$-C$_{12}$)alkyl, where portions of hydrogen on alkyl are replaced with fluorine, and (C$_6$-C$_{12}$) arylperfluoro(C$_1$-C$_{12}$)alkyl.

In another aspect of this invention there is also provided a photoimageable composition comprising:

a polymer capable of reacting with a carbene to form a carbene inserted product;

a compound of the formula (IA), (II) or (IIA):

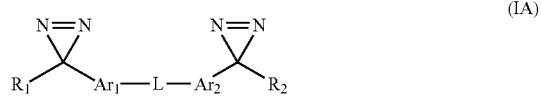

-continued

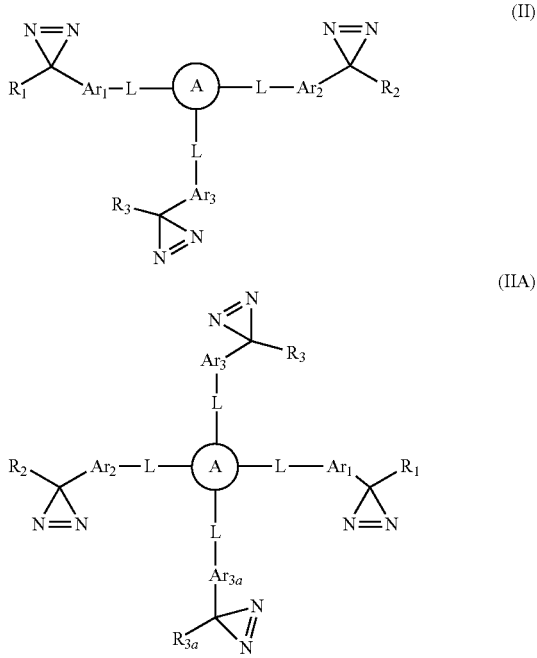

(II)

(IIA)

wherein,

L is a divalent linking or a spacer group selected from:
—C(O)O—R$_4$—OC(O)—, —C(O)O—R$_4$—, —R$_4$—OC(O)—R$_4$—, —C(O)—R$_4$—OC(O)—, —C(O)—R$_4$—, —R$_4$—C(O)—R$_4$—, —O—R$_4$—OC(O)—, —O—R$_4$—O—, —O—R$_4$—, —R$_4$—O—R$_4$—, —C(O)NR$_5$—R$_4$—OC(O)—, —C(O)NR$_5$—R$_4$—NR$_5$C(O)—, —C(O)NR$_5$—R$_4$—, —R$_4$—NR$_5$C(O)—R$_4$—, —C(O)—R$_4$—NR$_5$C(O)—, —NR$_5$—R$_4$—OC(O)—, —NR$_5$—R$_4$—NR$_5$C(O)—, —NR$_5$—R$_4$—, —R$_4$—NR$_5$—R$_4$—, —NR$_5$—R$_4$—NR$_5$—, —R$_4$—, and

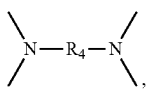

where each occurrence of R$_4$ may be the same or different which is a divalent group independently selected from (C$_1$-C$_{12}$)alkyl, (C$_3$-C$_{12}$)cycloalkyl, (C$_6$-C$_{12}$)aryl, (C$_6$-C$_{12}$)aryl(C$_1$-C$_{12}$)alkyl, (C$_6$-C$_{10}$)heteroaryl, (C$_6$-C$_{10}$)heteroaryl(C$_1$-C$_{12}$)alkyl, —(CH$_2$—CH$_2$—O)$_a$—, where a is an integer from 1 to 10, provided that when R$_4$ is —(CH$_2$—CH$_2$—O)$_a$— then the oxygen end of said group is linked only with either carbon or silicon containing linking group, which are optionally substituted with a group selected from halogen, —OH, (C$_1$-C$_4$)alkyl, (C$_1$-C$_4$)alkoxy, (C$_6$-C$_{10}$)aryl, (C$_6$-C$_{10}$)aryloxy, (C$_6$-C$_{12}$)aralkyl and (C$_6$-C$_{12}$)aralkyloxy; and R$_5$ is hydrogen, (C$_1$-C$_6$)alkyl, (C$_6$-C$_{10}$)aryl or (C$_6$-C$_{10}$)aralkyl;

A is a carbon, silicon, oxygen or nitrogen central core moiety;

R$_1$, R$_2$, R$_3$ and R$_{3a}$ are the same or different and each is independently selected from (C$_1$-C$_{12}$)alkyl, where portions of hydrogen on alkyl are replaced with fluorine, (C$_1$-C$_{12}$)perfluoroalkyl, (C$_6$-C$_{12}$)aryl, (C$_6$-C$_{12}$)aryl(C$_1$-C$_{12}$)alkyl, where portions of hydrogen on alkyl are replaced with fluorine, and (C$_6$-C$_{12}$)arylperfluoro(C$_1$-C$_{12}$)alkyl; and Ar$_1$, Ar$_2$ and Ar$_3$ are the same or different and each is independently selected from (C$_6$-C$_{12}$)arylene or (C$_6$-C$_{12}$)heteroarylene group optionally substituted with a group selected from halogen, —OH, (C$_1$-C$_4$)alkyl, (C$_1$-C$_4$)alkoxy, (C$_6$-C$_{10}$)aryl, (C$_6$-C$_{12}$)aryloxy, (C$_6$-C$_{12}$)aryl(C$_1$-C$_4$)alkyl and (C$_6$-C$_{12}$)aryl(C$_1$-C$_4$)alkyloxy; and a carrier solvent.

BRIEF DESCRIPTION OF THE DRAWINGS

Embodiments in accordance with the present invention are described below with reference to the following accompanying figures and/or images. Where drawings are provided, it will be drawings which are simplified portions of various embodiments of this invention and are provided for illustrative purposes only.

DETAILED DESCRIPTION

Figure 1:
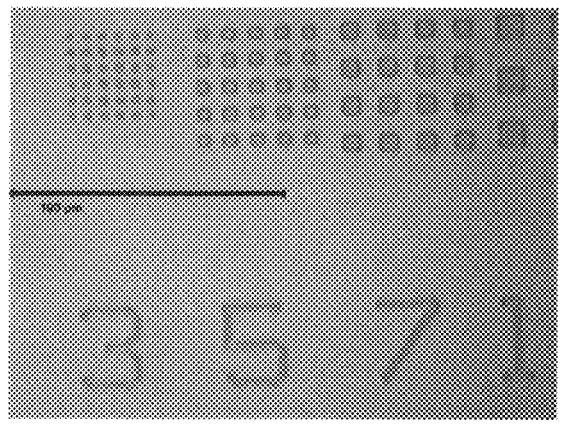
FIG. 1 is a lithographic image obtained for the composition of this invention containing the polymer, poly(HexNB) as set forth in Example 3 and the diazirine as set forth in Example 2.

The terms as used herein have the following meanings:

As used herein, the articles "a," "an," and "the" include plural referents unless otherwise expressly and unequivocally limited to one referent.

Since all numbers, values and/or expressions referring to quantities of ingredients, reaction conditions, etc., used herein and in the claims appended hereto, are subject to the various uncertainties of measurement encountered in obtaining such values, unless otherwise indicated, all are to be understood as modified in all instances by the term "about."

Where a numerical range is disclosed herein such range is continuous, inclusive of both the minimum and maximum values of the range as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all sub-ranges subsumed therein. For example, a stated range of from "1 to 10" should be considered to include any and all sub-ranges between the minimum value of 1 and the maximum value of 10. Exemplary sub-ranges of the range 1 to 10 include, but are not limited to, 1 to 6.1, 3.5 to 7.8, and 5.5 to 10, etc.

As used herein, the symbol "⌇" denotes a position at which the bonding takes place with another repeat unit or another atom or molecule or group or moiety as appropriate with the structure of the group as shown.

As used herein, "hydrocarbyl" refers to a group that contains carbon and hydrogen atoms, non-limiting examples being alkyl, cycloalkyl, aryl, aralkyl, alkaryl, and alkenyl.

The term "halohydrocarbyl" refers to a hydrocarbyl group where at least one hydrogen has been replaced by a halogen. The term perhalocarbyl refers to a hydrocarbyl group where all hydrogens have been replaced by a halogen.

As used herein, the expression "$(C_1-C_6)$alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$(C_1-C_4)$alkoxy", "$(C_1-C_4)$thioalkyl" "$(C_1-C_4)$alkoxy$(C_1-C_4)$alkyl", "hydroxy$(C_1-C_4)$alkyl", "$(C_1-C_4)$alkylcarbonyl", "$(C_1-C_4)$alkoxycarbonyl$(C_1-C_4)$alkyl", "$(C_1-C_4)$alkoxycarbonyl", "amino$(C_1-C_4)$alkyl", "$(C_1-C_4)$alkylamino", "$(C_1-C_4)$alkylcarbamoyl$(C_1-C_4)$alkyl", "$(C_1-C_4)$dialkylcarbamoyl$(C_1-C_4)$alkyl" "mono- or di-$(C_1-C_4)$alkylamino$(C_1-C_4)$alkyl", "amino$(C_1-C_4)$alkylcarbonyl" "diphenyl$(C_1-C_4)$alkyl", "phenyl$(C_1-C_4)$alkyl", "phenylcarboyl$(C_1-C_4)$alkyl" and "phenoxy$(C_1-C_4)$alkyl" are to be construed accordingly.

As used herein, the expression "cycloalkyl" includes all of the known cyclic groups. Representative examples of "cycloalkyl" includes without any limitation cyclopropyl, cyclobutyl, cyclopentyl, cyclohexyl, cycloheptyl, cyclooctyl, and the like. Derived expressions such as "cycloalkoxy", "cycloalkylalkyl", "cycloalkylaryl", "cycloalkylcarbonyl" are to be construed accordingly.

As used herein, the expression "$(C_2-C_6)$alkenyl" includes ethenyl and straight-chained or branched propenyl, butenyl, pentenyl and hexenyl groups. Similarly, the expression "$(C_2-C_6)$alkynyl" includes ethynyl and propynyl, and straight-chained or branched butynyl, pentynyl and hexynyl groups.

As used herein the expression "$(C_1-C_4)$acyl" shall have the same meaning as "$(C_1-C_4)$alkanoyl", which can also be represented structurally as "R—CO—," where R is a $(C_1-C_3)$alkyl as defined herein. Additionally, "$(C_1-C_3)$alkylcarbonyl" shall mean same as $(C_1-C_4)$acyl. Specifically, "$(C_1-C_4)$acyl" shall mean formyl, acetyl or ethanoyl, propanoyl, n-butanoyl, etc. Derived expressions such as "$(C_1-C_4)$acyloxy" and "$(C_1-C_4)$acyloxyalkyl" are to be construed accordingly.

As used herein, the expression "$(C_1-C_6)$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$(C_1-C_6)$perfluoroalkoxy", is to be construed accordingly. It should further be noted that certain of the alkyl groups as described herein, such as for example, "$(C_1-C_6)$alkyl" may partially be fluorinated, that is, only portions of the hydrogen atoms in said alkyl group are replaced with fluorine atoms and shall be construed accordingly.

As used herein, the expression "$(C_6-C_{10})$aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expression, "$(C_6-C_{10})$arylsulfonyl," is to be construed accordingly.

As used herein, the expression "$(C_6-C_{10})$aryl$(C_1-C_4)$alkyl" means that the $(C_6-C_{10})$aryl as defined herein is further attached to $(C_1-C_4)$alkyl as defined herein. Representative examples include benzyl, phenylethyl, 2-phenylpropyl, 1-naphthylmethyl, 2-naphthylmethyl and the like.

As used herein, the expression "heteroaryl" includes all of the known heteroatom containing aromatic radicals. Representative 5-membered heteroaryl radicals include furanyl, thienyl or thiophenyl, pyrrolyl, isopyrrolyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, cinnolyl, benzimidazolyl, indazolyl, pyridofuranyl, pyridothienyl, and the like radicals.

As used herein, the expression "heterocycle" includes all of the known reduced heteroatom containing cyclic radicals. Representative 5-membered heterocycle radicals include tetrahydrofuranyl, tetrahydrothiophenyl, pyrrolidinyl, 2-thiazolinyl, tetrahydrothiazolyl, tetrahydrooxazolyl, and the like. Representative 6-membered heterocycle radicals include piperidinyl, piperazinyl, morpholinyl, thiomorpholinyl, and the like. Various other heterocycle radicals include, without limitation, aziridinyl, azepanyl, diazepanyl, diazabicyclo[2.2.1]hept-2-yl, and triazocanyl, and the like.

"Halogen" or "halo" means chloro, fluoro, bromo, and iodo.

In a broad sense, the term "substituted" is contemplated to include all permissible substituents of organic compounds. In a few of the specific embodiments as disclosed herein, the term "substituted" means substituted with one or more substituents independently selected from the group consisting of $C_{1-6}$ alkyl, $C_{2-6}$alkenyl, $C_{1-6}$perfluoroalkyl, phenyl, hydroxy, —$CO_2H$, an ester, an amide, $C_1-C_6$alkoxy, $C_1-C_6$thioalkyl, $C_1-C_6$perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

It should be noted that any atom with unsatisfied valences in the text, schemes, examples and tables herein is assumed to have the appropriate number of hydrogen atom(s) to satisfy such valences.

As used herein, the terms "orthogonal" and "orthogonality" will be understood to mean chemical orthogonality. For example, an orthogonal solvent means a solvent which, when used in the deposition of a layer of a material dissolved therein on a previously deposited layer, does not dissolve said previously deposited layer.

As used herein, the term "organic semiconductor (OSC) composition", also shortly referred to as "composition", means at least one organic semiconductor (OSC) compound and one or more other materials added to the at least one OSC compound to provide, or to modify, specific properties of the OSC composition and/or of the at least one OSC compound therein. It will be understood that an OSC composition is also a vehicle for carrying the OSC to a substrate to enable the forming of layers or structures thereon. Exemplary materials include, but are not limited to, solvents, volatile surfactants and adhesion promoters.

As used herein, the terms "polymer composition," "copolymer composition," "terpolymer composition" or "tetrapolymer composition" are used herein interchangeably and are meant to include at least one synthesized polymer, copolymer, terpolymer or tetrapolymer, as well as residues from initiators, solvents or other elements attendant to the synthesis of such polymers, where such residues are understood as not necessarily being covalently incorporated thereto. But some catalysts or initiators may sometimes be covalently bound to a part of the polymeric chain either at the beginning and/or end of the polymeric chain. Such residues and other elements considered as part of the "polymer" or "polymer composition" are typically mixed or co-mingled with the polymer such that they tend to remain therewith when it is transferred between vessels or between solvent or dispersion media. A polymer composition can also include materials added after synthesis of the polymer to provide or modify specific properties of such composition. Such materials include, but are not limited to solvent(s), antioxidant(s), photoinitiator(s), sensitizers and other materials as will be discussed more fully below.

By the term, "a monomer repeat unit is derived" is meant that the polymeric repeating units are polymerized (formed) from, e.g., polycyclic norbornene-type monomers, wherein the resulting polymers are formed by 2,3 enchainment of norbornene-type monomers as shown below:

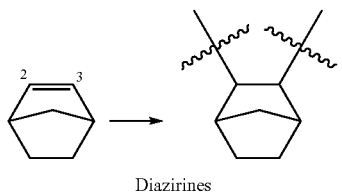

Diazirines

Thus, in accordance with the practice of this invention there is provided a compound of the formula (I):

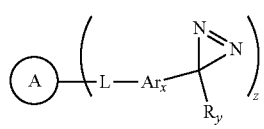

Wherein, A is a carbon, silicon, oxygen or nitrogen central core moiety;

L is a bond or a divalent linking or a spacer group selected from ether, ketone, amine, sulfide, sulfone, ester, amide or a combination thereof; $Ar_x$ is an aromatic or heteroaromatic group and $R_y$ is an alkyl, aryl, arylalkyl, partly fluorinated or perfluorinated alkyl, aryl and arylalkyl group; and z is an integer from 2 to 4. Non-limiting examples of central core moiety A can be selected from aliphatic, cycloaliphatic, heteroaliphatic, heterocycloaliphatic, aromatic or heteroaromatic moieties.

In another aspect there is provided a compound of formula (IA):

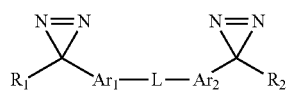

Wherein,

L is a bond or a divalent linking or a spacer group selected from:

—C(O)O—$R_4$—OC(O)—, —C(O)O—$R_4$—, —$R_4$—OC(O)—$R_4$—, —C(O)—$R_4$—OC(O)—, —C(O)—$R_4$—, —$R_4$—C(O)—$R_4$—, —O—$R_4$—OC(O)—, —O—$R_4$—O—, —O—$R_4$—, —C(O)NR_5—$R_4$—OC(O)—, —C(O)NR_5—$R_4$—NR_5C(O)—, —C(O)NR_5—$R_4$—, —$R_4$—NR_5C(O)—$R_4$—, —C(O)—$R_4$—NR_5C(O)—, —NR_5—$R_4$—OC(O)—, —NR_5—$R_4$—NR_5C(O)—, —NR_5—$R_4$—, —$R_4$—NR_5—$R_4$—, —NR_5—$R_4$—NR_5—

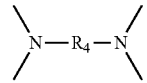

and —$R_4$—, where each occurrence of $R_4$ may be the same or different which is a divalent group independently selected from $(C_1-C_{12})$alkyl, $(C_3-C_{12})$cycloalkyl, $(C_6-C_{12})$aryl, $(C_6-C_{12})$aryl$(C_1-C_{12})$alkyl, $(C_6-C_{10})$heteroaryl, $(C_6-C_{10})$heteroaryl$(C_1-C_{12})$alkyl, —(CH$_2$—CH$_2$—O)$_a$—, where a is an integer from 1 to 10, provided that when $R_4$ is —(CH$_2$—CH$_2$—O)$_a$— then the oxygen end of said group is linked only with either carbon or silicon containing linking group, which are optionally substituted with a group selected from halogen, —OH, $(C_1-C_4)$alkyl, $(C_1-C_4)$alkoxy, $(C_6-C_{10})$aryl, $(C_6-C_{10})$aryloxy, $(C_6-C_{12})$aralkyl and $(C_6-C_{12})$aralkyloxy; and $R_5$ is hydrogen, $(C_1-C_6)$alkyl, $(C_6-C_{10})$aryl or $(C_6-C_{10})$aralkyl;

$R_1$ and $R_2$ are the same or different and each is independently selected from $(C_1-C_{12})$alkyl, where portions of hydrogen on alkyl are replaced with fluorine, $(C_1-C_{12})$perfluoroalkyl, $(C_6-C_{12})$aryl, $(C_6-C_{12})$aryl$(C_1-C_{12})$alkyl, where portions of hydrogen on alkyl are replaced with fluorine, and $(C_6-C_{12})$arylperfluoro$(C_1-C_{12})$alkyl; and $Ar_1$ and $Ar_2$ are the same or different and each is independently selected from $(C_6-C_{12})$arylene or $(C_6-C_{12})$heteroarylene group optionally substituted with a group selected from halogen, —OH, $(C_1-C_4)$alkyl, $(C_1-C_4)$alkoxy, $(C_6-C_{10})$aryl, $(C_6-C_{12})$aryloxy, $(C_6-C_{12})$aryl$(C_1-C_4)$alkyl and $(C_6-C_{12})$aryl$(C_1-C_4)$alkyloxy; and with the proviso that the following compounds are excluded:

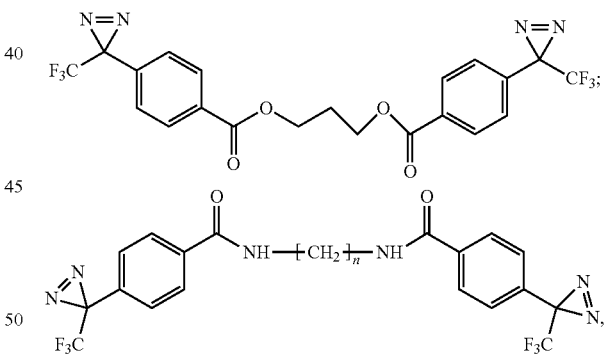

where n is 7 or 12; and

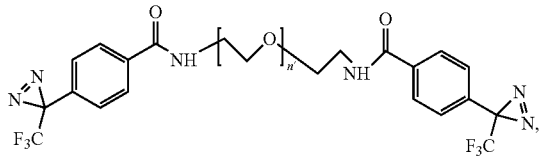

where n' is 3 or 5.

In another aspect of this invention there is also provided a compound of formula (II) or (IIA):

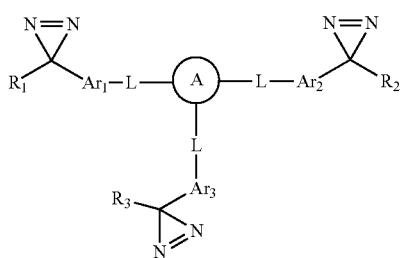

(II)

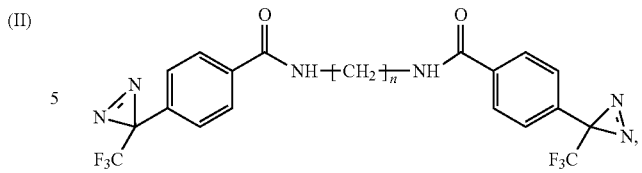

where n is 7 or 12;

As well as well as some of the amido ethers of formula:

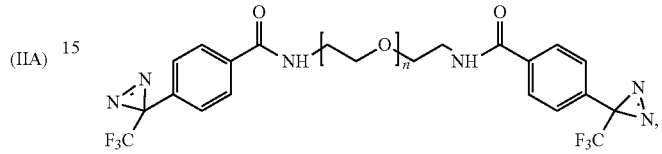

where n is 3 or 5.

Accordingly, the above noted compounds are excluded from this invention.

In one of the embodiments of this invention, the compound of the formula (IA), (II) or (IIA) encompasses the following:

L is a linking group selected from:
—C(O)O—(CH$_2$)$_b$—O(CO)—, —C(O)O—(CH$_2$)$_b$—, —(CH$_2$)$_b$—O(CO)—(CH$_2$)$_b$—, —C(O)—(CH$_2$)$_b$—O(CO)—, —C(O)—(CH$_2$)$_b$—, —(CH$_2$)$_b$—(CO)—(CH$_2$)$_b$—, —O—(CH$_2$)$_b$—O(CO)—, —O—(CH$_2$)$_b$—O—, —O—(CH$_2$)$_b$—, —(CH$_2$)$_b$—O—(CH$_2$)$_b$—, —C(O)NR$_5$—(CH$_2$)$_b$—O(CO)—, —C(O)NR$_5$—(CH$_2$)$_b$—NR$_5$(CO)—, —C(O)NR$_5$—(CH$_2$)$_b$—, —(CH$_2$)$_b$—NR$_5$(CO)—(CH$_2$)$_b$—, —C(O)—(CH$_2$)$_b$—NR$_5$(CO)—, —NR$_5$—(CH$_2$)$_b$—O(CO)—, —NR$_5$—(CH$_2$)$_b$—NR$_5$(CO)—, —NR$_5$—(CH$_2$)$_b$—, —(CH$_2$)$_b$—NR$_5$—(CH$_2$)$_b$—, —NR$_5$—(CH$_2$)$_b$—NR$_5$— where b is an integer from 1 to 12;

R$_5$ is hydrogen, (C$_1$-C$_4$)alkyl, phenyl, naphthyl, tolyl or benzyl;

R$_1$, R$_2$, R$_3$ and R$_{3a}$ are the same or different and each independently selected from (C$_1$-C$_6$)alkyl, (C$_1$-C$_6$)perfluoroalkyl, (C$_6$-C$_8$)aryl, (C$_6$-C$_8$)perfluoroaryl, (C$_6$-C$_{10}$)aralkyl or (C$_6$-C$_{10}$)perfluoroarylperfluoroalkyl; and Ar$_1$, Ar$_2$, Ar$_3$ and Ar$_{3a}$ are the same or different and are independently of each other selected from phenylene or naphthalene group optionally substituted with a group selected from halogen, —OH, (C$_1$-C$_4$)alkyl, (C$_1$-C$_4$)alkoxy, (C$_6$-C$_{10}$)aryl, (C$_6$-C$_{10}$)aryloxy, (C$_6$-C$_{12}$)aralkyl and (C$_6$-C$_{12}$)aralkyloxy.

In one of the embodiments of this invention, the compound of the formula (II) or (IIA) encompasses the following:

L is a linking group selected from:
—C(O)O—(CH$_2$)$_b$—O(CO)—, —C(O)O—(CH$_2$)$_b$—, —(CH$_2$)$_b$—O(CO)—(CH$_2$)$_b$—, —C(O)—(CH$_2$)$_b$—O(CO)—, —C(O)—(CH$_2$)$_b$—, —(CH$_2$)$_b$—(CO)—(CH$_2$)$_b$—, —O—(CH$_2$)$_b$—O(CO)—, —O—(CH$_2$)$_b$—O—, —O—(CH$_2$)$_b$—, —(CH$_2$)$_b$—O—(CH$_2$)$_b$—, —C(O)NR$_5$—(CH$_2$)$_b$—O(CO)—, —C(O)NR$_5$—(CH$_2$)$_b$—NR$_5$(CO)—, —C(O)NR$_5$—(CH$_2$)$_b$—, —(CH$_2$)$_b$—NR$_5$(CO)—(CH$_2$)$_b$—, —C(O)—(CH$_2$)$_b$—NR$_5$(CO)—, —NR$_5$—(CH$_2$)$_b$—O(CO)—, —NR$_5$—(CH$_2$)$_b$—NR$_5$(CO)—, —NR$_5$—(CH$_2$)$_b$—, —(CH$_2$)$_b$—NR$_5$—(CH$_2$)$_b$—, —NR$_5$—

(IIA)

Where L, A, Ar$_1$, Ar$_2$, R$_1$ and R$_2$ are as defined herein. Ar$_3$ and Ar$_{3a}$ may be the same as Ar$_1$ and Ar$_2$ and are independently of each other selected from (C$_6$-C$_{12}$)arylene or (C$_6$-C$_{12}$)heteroarylene group optionally substituted with a group selected from halogen, —OH, (C$_1$-C$_4$)alkyl, (C$_1$-C$_4$)alkoxy, (C$_6$-C$_{10}$)aryl, (C$_6$-C$_{12}$)aryloxy, (C$_6$-C$_{12}$)aryl(C$_1$-C$_4$)alkyl and (C$_6$-C$_{12}$)aryl(C$_1$-C$_4$)alkyloxy. Similarly, R$_3$ and R$_{3a}$ may be the same as R$_1$ and R$_2$ and are independently of each other selected from (C$_1$-C$_{12}$)alkyl, where portions of hydrogen on alkyl are replaced with fluorine, (C$_1$-C$_{12}$)perfluoroalkyl, (C$_6$-C$_{12}$)aryl, (C$_6$-C$_{12}$)aryl(C$_1$-C$_{12}$)alkyl, where portions of hydrogen on alkyl are replaced with fluorine, and (C$_6$-C$_{12}$)arylperfluoro(C$_1$-C$_{12}$)alkyl.

As noted above, a few of the compounds of formula (I) are known in the literature and such compounds are excluded from this aspect of the invention. For example, K. Simonton et al., RadTech e/5, 2006, Technical Proceedings, disclose a bifunctional diazirine of formula:

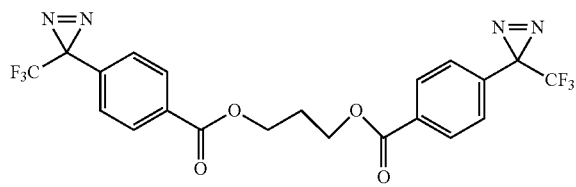 [SMILES: O=C(OCCCOC(=O)c1ccc(C2(C(F)(F)F)N=N2)cc1)c1ccc(C2(C(F)(F)F)N=N2)cc1]

Propane-1,3-diyl bis(4-(3-(trifluoromethyl)-3H-diazirin-3-yl)benzoate). Similarly, H. Mehenni et al., Aust. J. Chem. 2012, 65, 193-201, disclose a series of bis(diazirines) including the bis(diazirine) diamides of formula:

(CH$_2$)$_b$—NR$_5$— where b is an integer from 1 to 10; R$_5$ is hydrogen, (C$_1$-C$_4$)alkyl, phenyl, naphthyl, tolyl or benzyl;

R$_1$, R$_2$, R$_3$ and R$_{3a}$ are the same or different and each independently selected from (C$_1$-C$_6$)alkyl, (C$_1$-C$_6$)perfluoroalkyl, (C$_6$-C$_8$)aryl, (C$_6$-C$_8$)perfluoroaryl, (C$_6$-C$_{10}$)aralkyl or (C$_6$-C$_{10}$)perfluoroarylperfluoroalkyl; and Ar$_1$, Ar$_2$, Ar$_3$ and Ar$_{3a}$ are the same or different and are independently of each other selected from phenylene or naphthalene group optionally substituted with a group selected from halogen, —OH, (C$_1$-C$_4$)alkyl, (C$_1$-C$_4$)alkoxy, (C$_6$-C$_{10}$)aryl, (C$_6$-C$_{10}$)aryloxy, (C$_6$-C$_{12}$)aralkyl and (C$_6$-C$_{12}$)aralkyloxy.

In yet another embodiment of this invention, the compound of the formula (IA), (II) or (IIA) encompasses the following:

L is a linking group selected from:
—C(O)O—(CH$_2$)$_b$—O(CO)—, —C(O)O—(CH$_2$)$_b$—, —(CH$_2$)$_b$—O(CO)—(CH$_2$)$_b$—, —O—(CH$_2$)$_b$—O—, —O—(CH$_2$)$_b$—, —(CH$_2$)$_b$—O—(CH$_2$)$_b$—, —C(O)NR$_5$—(CH$_2$)$_b$—NR$_5$(CO)—, —NR$_5$—(CH$_2$)$_b$—, —(CH$_2$)$_b$—NR$_5$—(CH$_2$)$_b$—, —NR$_5$—(CH$_2$)$_b$—NR$_5$— where b is an integer from 1 to 6; R$_5$ is hydrogen, methyl, ethyl, propyl, isopropyl, n-butyl, tert-butyl, phenyl, naphthyl, tolyl or benzyl;

R$_1$, R$_2$, R$_3$ and R$_{3a}$ are the same or different and each independently selected from methyl, ethyl, propyl, isopropyl, n-butyl, tert-butyl, trifluoromethyl, pentafluoroethyl, heptafluoropropyl, phenyl, pentafluorophenyl, benzyl or heptafluorobenzyl; and Ar$_1$, Ar$_2$, Ar$_3$ and Ar$_{3a}$ are the same or different and are independently of each other selected from phenylene or naphthalene group optionally substituted with a group selected from fluorine, methyl, ethyl, propyl, isopropyl, n-butyl, tert-butyl, methoxy, ethoxy, propoxy, isopropoxy, n-butoxy, tert-butoxy, phenyl, naphthyl, tolyl, benzyl, phenoxy, naphthyloxy, tolyloxy or benzyloxy.

In yet another embodiment of this invention, the compound of the formula (II) or (IIA) encompasses the following:

L is a linking group selected from:
—C(O)O(CH$_2$)$_b$—O(CO)—, —C(O)O—(CH$_2$)$_b$—, —(CH$_2$)$_b$—O(CO)—(CH$_2$)$_b$—, —O—(CH$_2$)$_b$—O—, —O—(CH$_2$)$_b$—, —(CH$_2$)$_b$—O—(CH$_2$)$_b$—, —C(O)NR$_5$—(CH$_2$)$_b$—NR$_5$(CO)—, —NR$_5$—(CH$_2$)$_b$—, —(CH$_2$)$_b$—NR$_5$—(CH$_2$)$_b$—, —NR$_5$—(CH$_2$)$_b$—NR$_5$— where b is an integer from 2 to 6; R$_5$ is hydrogen, methyl, ethyl, propyl, isopropyl, n-butyl, tert-butyl, phenyl, naphthyl, tolyl or benzyl;

R$_1$, R$_2$, R$_3$ and R$_{3a}$ are the same or different and each independently selected from methyl, ethyl, propyl, isopropyl, n-butyl, tert-butyl, trifluoromethyl, pentafluoroethyl, heptafluoropropyl, phenyl, pentafluorophenyl, benzyl or heptafluorobenzyl; and Ar$_1$, Ar$_2$, Ar$_3$ and Ar$_{3a}$ are the same or different and are independently of each other selected from phenylene or naphthalene group optionally substituted with a group selected from fluorine, methyl, ethyl, propyl, isopropyl, n-butyl, tert-butyl, methoxy, ethoxy, propoxy, isopropoxy, n-butoxy, tert-butoxy, phenyl, naphthyl, tolyl, benzyl, phenoxy, naphthyloxy, tolyloxy or benzyloxy.

Non-limiting representative examples of the compounds encompassed by the compound of formula (IA) may be selected from the group consisting of the following:

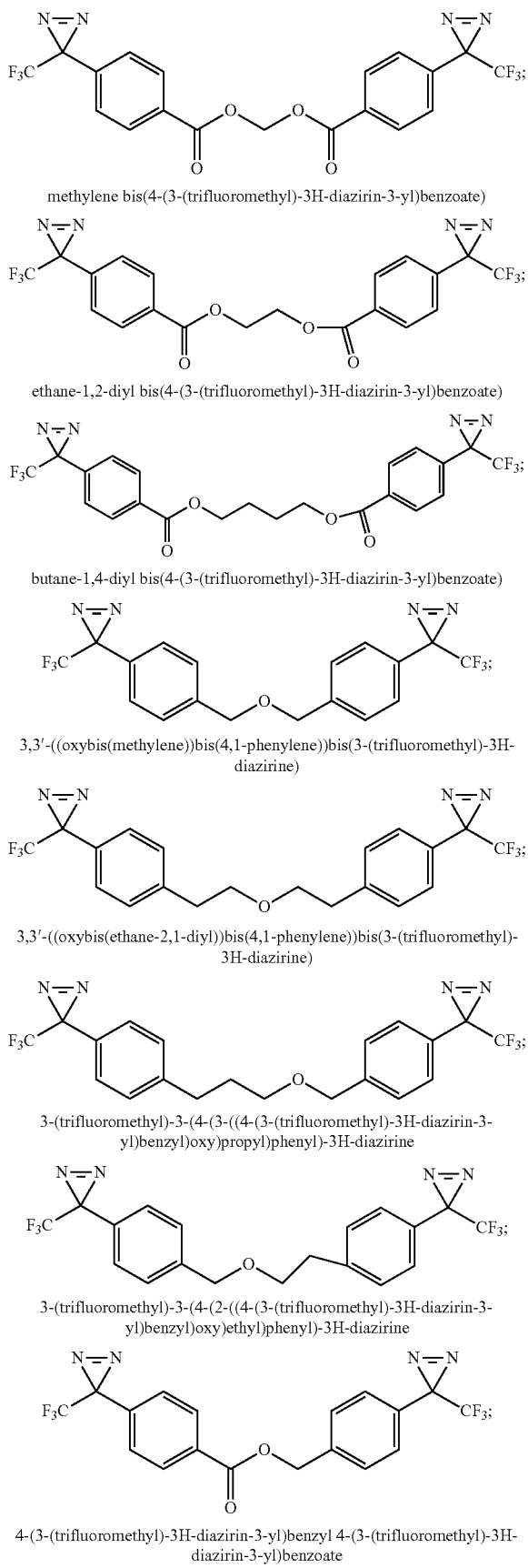

methylene bis(4-(3-(trifluoromethyl)-3H-diazirin-3-yl)benzoate)

ethane-1,2-diyl bis(4-(3-(trifluoromethyl)-3H-diazirin-3-yl)benzoate)

butane-1,4-diyl bis(4-(3-(trifluoromethyl)-3H-diazirin-3-yl)benzoate)

3,3'-((oxybis(methylene))bis(4,1-phenylene))bis(3-(trifluoromethyl)-3H-diazirine)

3,3'-((oxybis(ethane-2,1-diyl))bis(4,1-phenylene))bis(3-(trifluoromethyl)-3H-diazirine)

3-(trifluoromethyl)-3-(4-(3-((4-(3-(trifluoromethyl)-3H-diazirin-3-yl)benzyl)oxy)propyl)phenyl)-3H-diazirine 3-(trifluoromethyl)-3-(4-(2-((4-(3-(trifluoromethyl)-3H-diazirin-3-yl)benzyl)oxy)ethyl)phenyl)-3H-diazirine 4-(3-(trifluoromethyl)-3H-diazirin-3-yl)benzyl 4-(3-(trifluoromethyl)-3H-diazirin-3-yl)benzoate

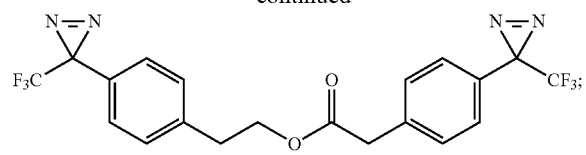

4-(3-(trifluoromethyl)-3H-diazirin-3-yl)phenethyl 2-(4-(3-(trifluoromethyl)-3H-diazirin-3-yl)phenyl)acetate

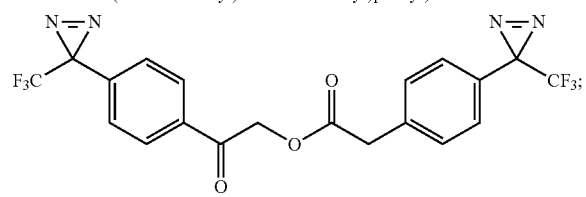

2-oxo-2-(4-(3-(trifluoromethyl)-3H-diazirin-3-yl)phenyl)ethyl 3-(3-(trifluoromethyl)-3H-diazirin-3-yl)benzoate

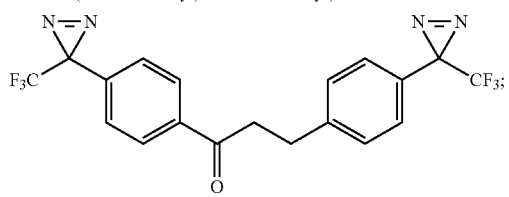

1,3-bis(4-(3-(trifluoromethyl)-3H-diazirin-3-yl)phenyl)propan-1-one

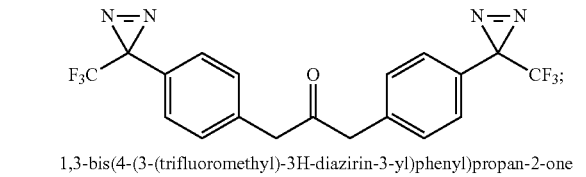

1,3-bis(4-(3-(trifluoromethyl)-3H-diazirin-3-yl)phenyl)propan-2-one

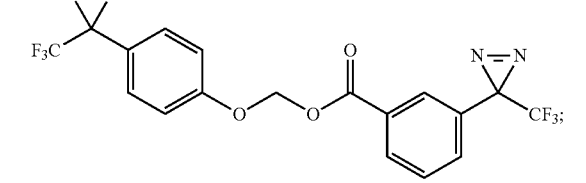

(4-(3-(trifluoromethyl)-3H-diazirin-3-yl)phenoxy)methyl 3-(3-(trifluoromethyl)-3H-diazirin-3-yl)benzoate

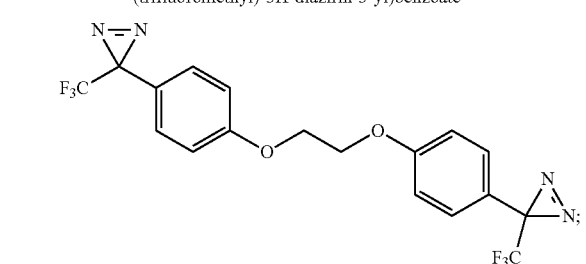

1,2-bis(4-(3-(trifluoromethyl)-3H-diazirin-3-yl)phenoxy)ethane

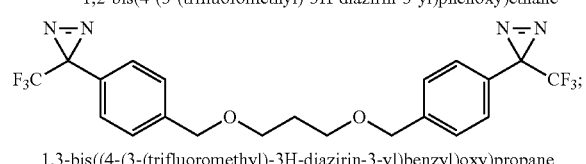

1,3-bis((4-(3-(trifluoromethyl)-3H-diazirin-3-yl)benzyl)oxy)propane

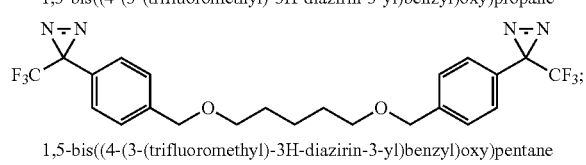

1,5-bis((4-(3-(trifluoromethyl)-3H-diazirin-3-yl)benzyl)oxy)pentane

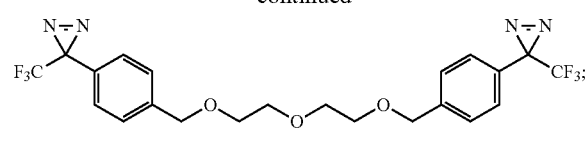

3,3'-((((oxybis(ethane-2,1-diyl))bis(oxy))bis(methylene))bis(4,1-phenylene))bis(3-(trifluoromethy)-3H-diazirine)

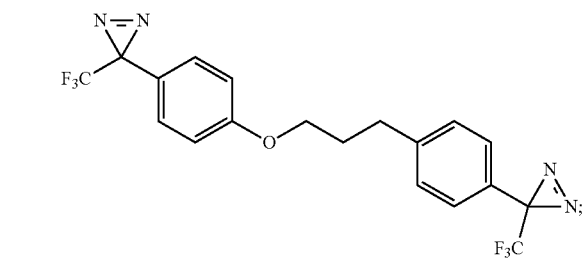

3-(trifluoromethyl)-3-(4-(3-(4-(3-(trifluoromethyl)-3H-diazirin-3-yl)phenoxy)propyl)phenyl)-3H-diazirine

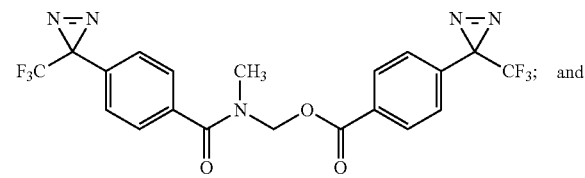

(N-methyl-4-(3-(trifluoromethyl)-3H-diazirin-3-yl)benzamido)methyl 4-(3-(trifluoromethyl)-3H-diazirin-3-yl)benzoate

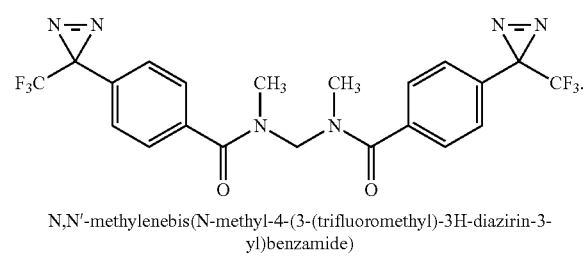

N,N'-methylenebis(N-methyl-4-(3-(trifluoromethyl)-3H-diazirin-3-yl)benzamide)

In a further embodiment the compounds within the scope of compound of formula (I), without any limitation, are selected from the group consisting of the following:

methylene bis(4-(3-(trifluoromethyl)-3H-diazirin-3-yl)benzoate

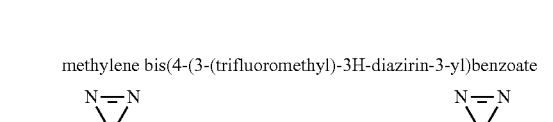

3,3'-((oxybis(methylene))bis(4,1-phenylene))bis(3-(trifluoromethyl)-3H-diazirine)

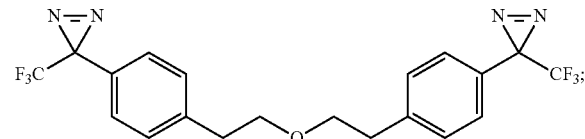

3,3'-((oxybis(ethane-2,1-diyl))bis(4,1-phenylene))bis(3-(trifluoromethyl)-3H-diazirine)

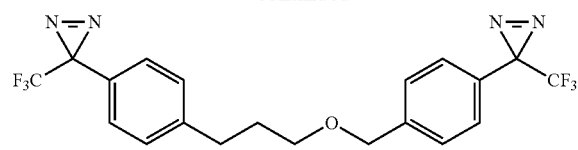

3-(trifluoromethyl)-3-(4-(3-((4-(3-(trifluoromethyl)-3H-diazirine-3-yl)benzyl)oxy)propyl)phenyl)-3H-diazirine

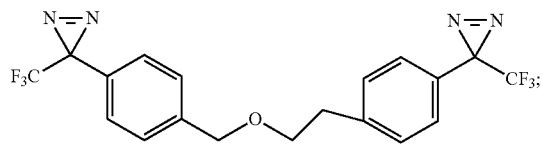

3-(trifluoromethyl)-3-(4-(2-((4-(3-(trifluoromethyl)-3H-diazirin-3-yl)benzyl)oxy)ethyl)phenyl)-3H-diazirine

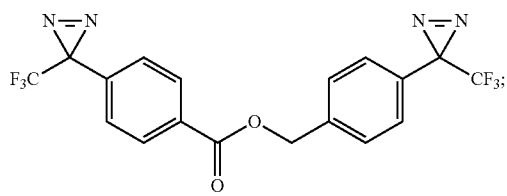

4-(3-(trifluoromethyl)-3H-diazirin-3-yl)benzyl 4-(3-(trifluoromethyl)-3H-diazirin-3-yl)benzoate

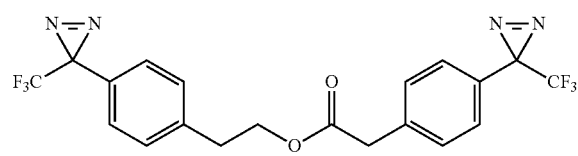

4-(3-(trifluoromethyl)-3H-diazirin-3-yl)phenethyl 2-(4-(3-(trifluoromethyl)-3H-diazirin-3-yl)phenyl)acetate

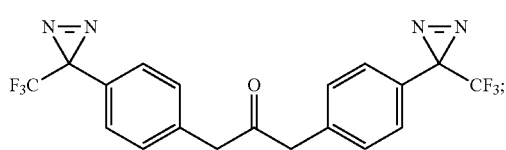

1,3-bis(4-(3-(trifluoromethyl)-3H-diazirin-3-yl)phenyl)propan-2-one

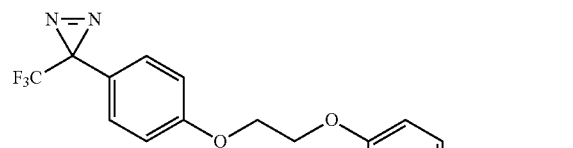

1,2-bis(4-(3-(trifluoromethyl)-3H-diazirin-3-yl)phenoxy)ethane

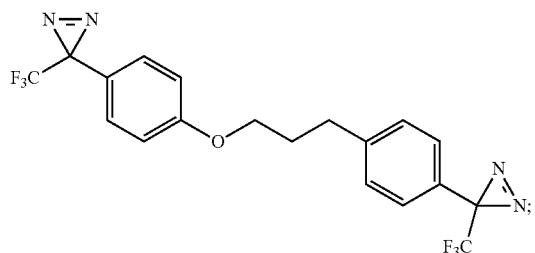

3-(trifluoromethyl)-3-(4-(3-(4-(3-(trifluoromethyl)-3H-diazirin-3-yl)phenoxy)propyl)phenyl)-3H-diazirine

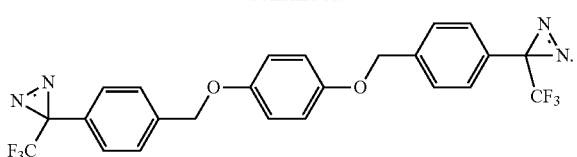

1,4-bis((4-(3-(trifluoromethyl)-3H-diazirin-3-yl)benzyl)oxy)benzene

In another embodiment, non-limiting examples of the compounds encompassed by the compound of formula (II) or (IIA) are selected from the group consisting of:

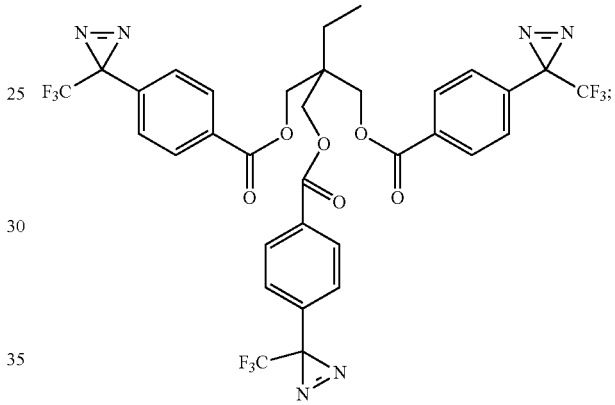

2-ethyl-2-(((4-(3-(trifluoromethyl)-3H-diazirin-3-yl)benzoyl)oxy)methyl)propane-1,3-diyl bis(4-(3-(trifluoromethyl)-3H-diazirin-3yl)benzoate)

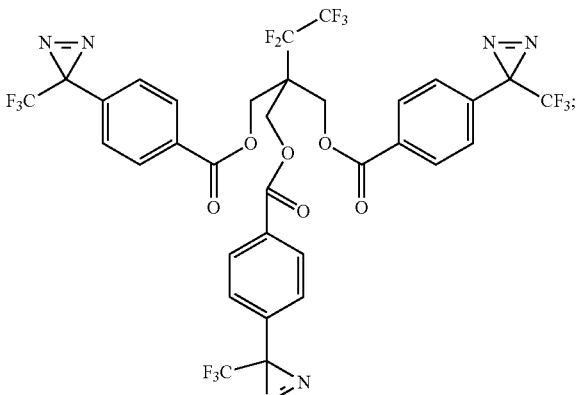

2-(perfluoroethyl)-2-(((4-(3-(trifluoromethyl)-3H-diazirin-3-yl)benzoyl)oxy)methyl)propane-1,3-diyl bis(4-(3-(trifluoromethyl)-3H-diazirin-3-yl)benzoate)

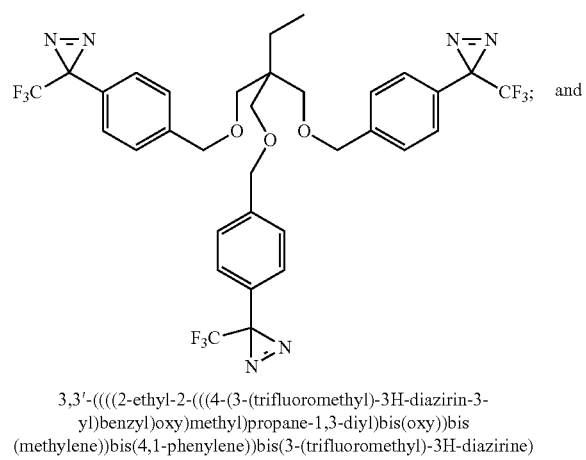

3,3'-((((2-ethyl-2-(((4-(3-(trifluoromethyl)-3H-diazirin-3-yl)benzyl)oxy)methyl)propane-1,3-diyl)bis(oxy)bis(methylene))bis(4,1-phenylene))bis(3-(trifluoromethyl)-3H-diazirine)

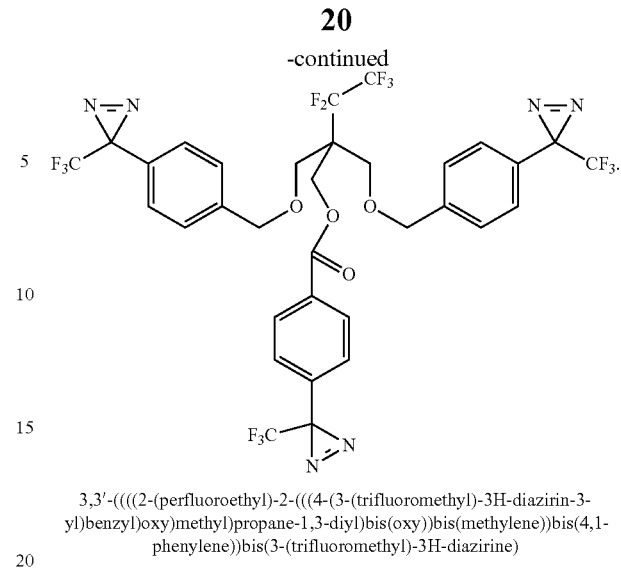

3,3'-((((2-(perfluoroethyl)-2-(((4-(3-(trifluoromethyl)-3H-diazirin-3-yl)benzyl)oxy)methyl)propane-1,3-diyl)bis(oxy))bis(methylene))bis(4,1-phenylene))bis(3-(trifluoromethyl)-3H-diazirine)

In a further embodiment of this invention non-limiting examples of diazirine compounds of this invention may be enumerated as follows:

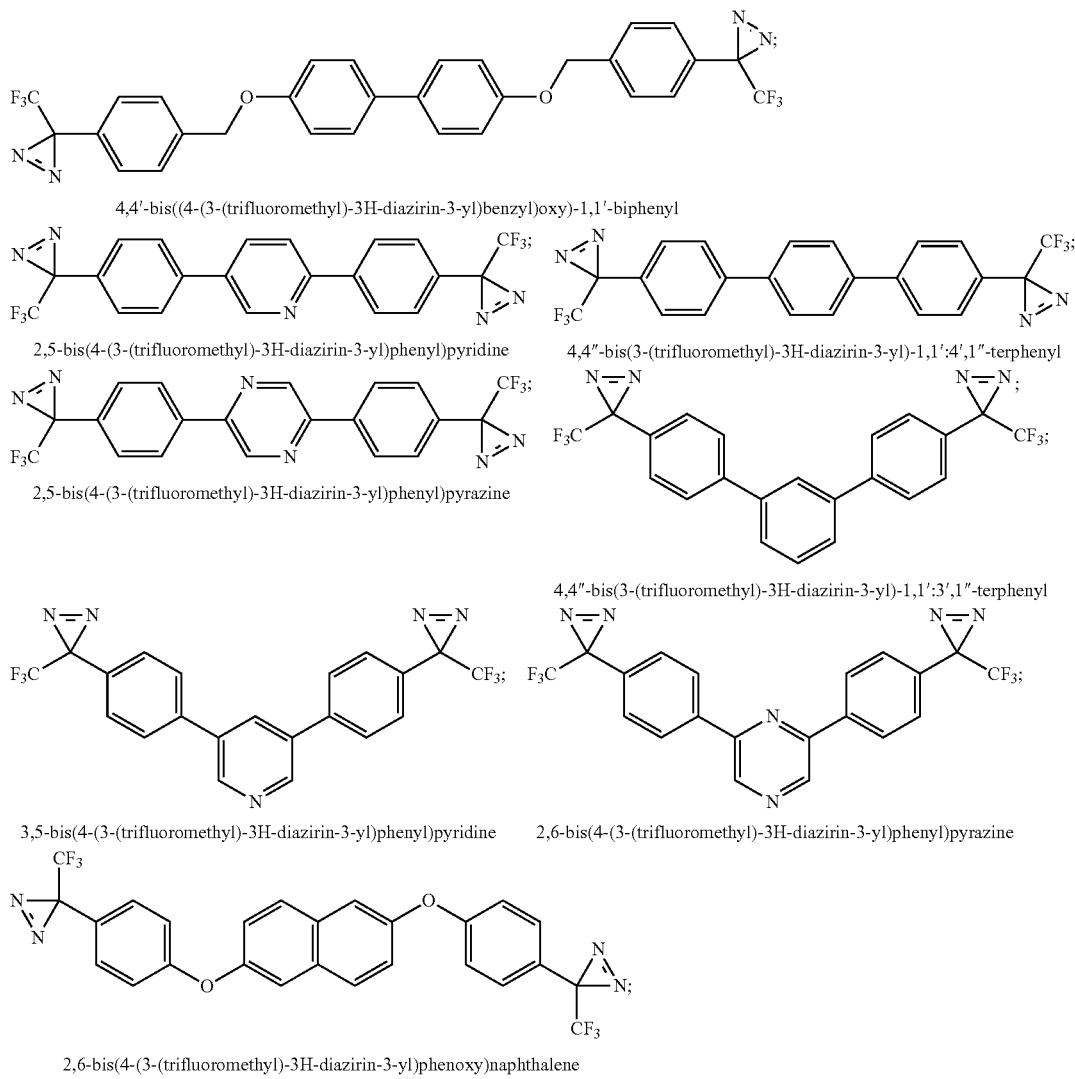

-continued
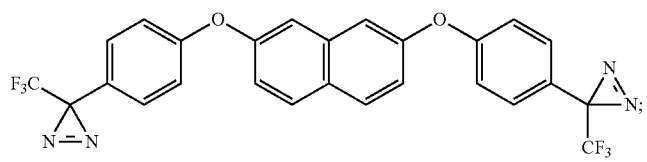
2,7-bis(4-(3-(trifluoromethyl)-3H-diazirin-3-yl)phenoxy)naphthalene
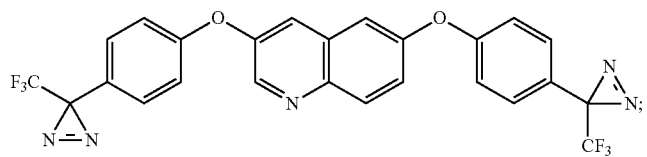
3,6-bis(4-(3-(trifluoromethyl)-3H-diazirin-3-yl)phenoxy)quinoline
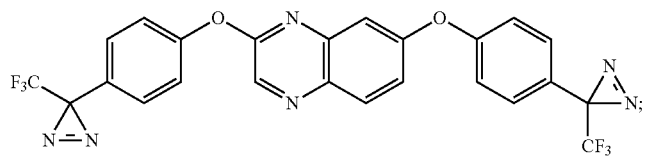
2,7-bis(4-(3-(trifluoromethyl)-3H-diazirin-3-yl)phenoxy)quinoxaline
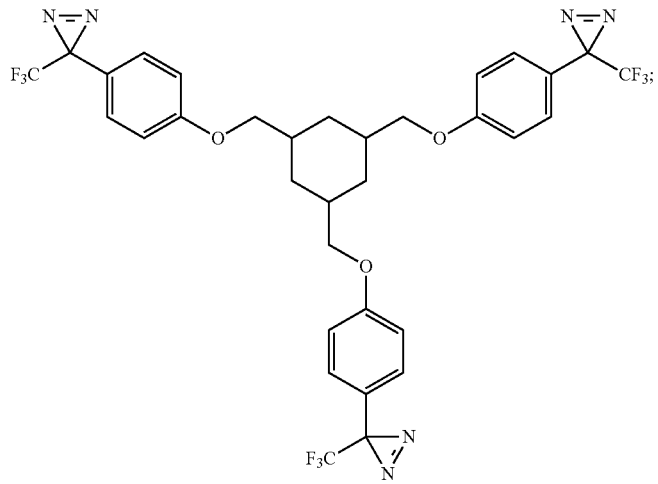
1,3,5-tris((4-(3-(trifluoromethyl)-3H-diazirin-3-yl)phenoxy)methyl)cyclohexane
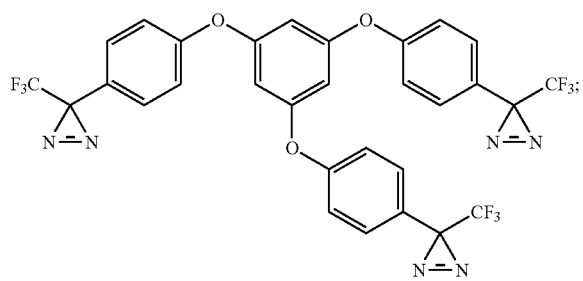
1,3,5-tris(4-(3-(trifluoromethyl)-3H-diazirin-3-yl)phenoxy)benzene -continued

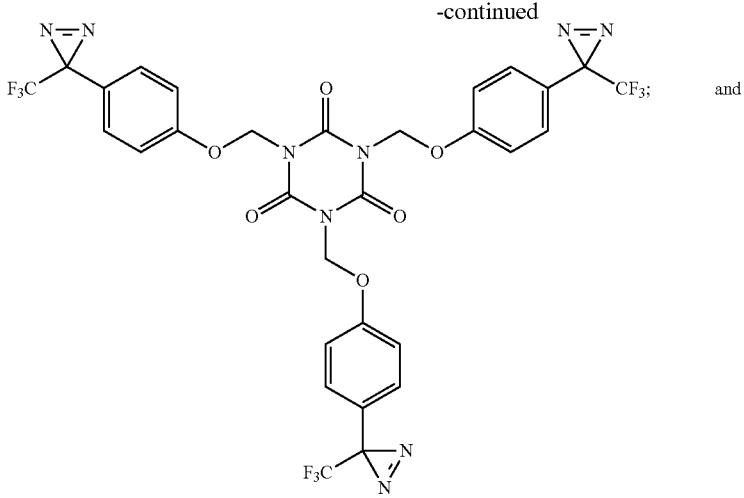

1,3,5-tris((4-(3-(trifluoromethyl)-3H-diazirin-3-yl)phenoxy)methyl)-1,3,5-triazinane-2,4,6-trione

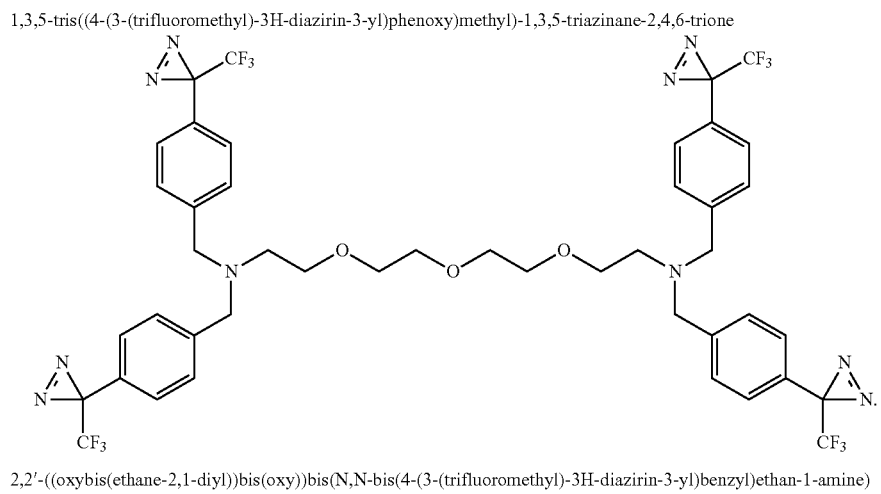

2,2'-((oxybis(ethane-2,1-diyl))bis(oxy))bis(N,N-bis(4-(3-(trifluoromethyl)-3H-diazirin-3-yl)benzyl)ethan-1-amine)

The compounds of this invention can be synthesized by any of the procedures known to one skilled in the art. Specifically, as noted above, a few of the compounds of formula (I), and several of the starting materials used in the preparation of the compounds of this invention are known or are themselves commercially available. The compounds of this invention and several of the precursor compounds may also be prepared by methods used to prepare similar compounds as reported in the literature and as further described herein. See for example, K. Simonton et al., RadTech e/5, 2006, Technical Proceedings; and H. Mehenni et al., Aust. J. Chem. 2012, 65, 193-201; pertinent portions of all of which are incorporated herein by reference.

More specifically, the compounds disclosed herein can be synthesized according to the following procedures of Schemes 1-2, wherein $R_1$, $R_4$ are as defined for formula (I), $R_2$ is same as $R_1$, and $Ar_1$ and $Ar_2$ are both phenyl and L is —C(O)O—$R_4$—O(CO)— in Scheme 1, represented as a compound of formula (IB). In Scheme 2, L is —$R_4$—O—$R_4$—, and all other substituents are same as in Scheme 1. Similar procedures can be employed for preparing the compounds of formula (II). In addition, similar procedures and/or other procedures known in the art can be used to make various other compounds of formula (I) or (II) where other L, $R_3$, $Ar_1$, $Ar_2$ and $Ar_3$ groups as defined herein are employed.

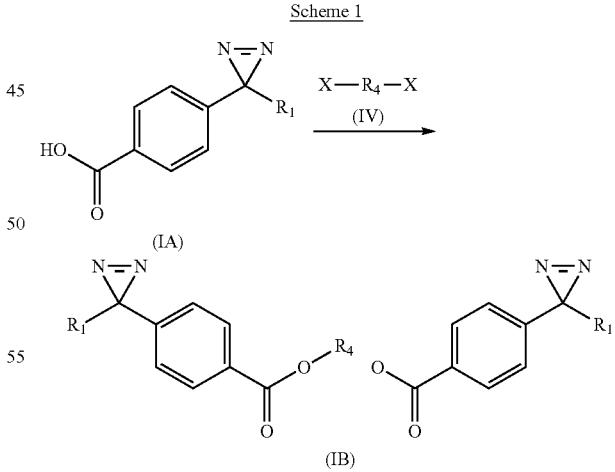

Scheme 1

In Scheme 1, the compound of formula (IA) is reacted with a compound of formula (IV), where X is a halogen (for example chlorine, bromine or iodine) or a leaving group such as mesylate, tosylate, acetate and the like. This reaction can be carried out by any of the procedures known in the art. For example, a solution of compound of formula (IA) can be reacted with a compound of formula (IV) where X is iodine in a suitable solvent in the presence of a suitable base. Suitable solvents include ketone solvents such as acetone or halogenated solvents such as dichloromethane and the like or mixtures in combination thereof. Suitable base include alkaline metal or alkaline earth metal carbonate or bicarbonate, such as sodium carbonate, potassium carbonate or ammonium carbonate, and the like. The reaction can be carried out at ambient, sub-ambient or super-ambient temperature conditions suitably in a dark or yellow light conditions to ensure that the diazirine group is not affected. Generally, the reaction temperature can range from about −20° C. to 60° C., but higher temperatures can be employed depending upon the type of bis-, tris- or tetrakis-diazirines that are being made.

As noted, Scheme 2 further illustrates preparation of the compounds of this invention, a compound of formula (IE), where L is a —R$_4$—O—R$_4$—. Again, any of the known procedures and/or variations thereof can be employed to prepare compounds of formula (IE). In Scheme 2, the compound of formula (IC) is reacted with a compound of formula (ID) under suitable reaction conditions to form the compound of formula (IE). Typically, such reactions are carried out in the presence of ether solvents such as tetrahydrofuran (THF) or diethyl ether in the presence of a suitable base or an alkaline metal to form the alkaline metal salt of the compound of formula (IC) which is then reacted with a compound of formula (ID), where X is a halogen (for example chlorine, bromine or iodine) or a leaving group such as mesylate, tosylate, acetate and the like. For example, a compound of formula (IC) in a solvent, such as THF can be reacted with sodium hydride to form the corresponding sodium salt, which is then reacted with a compound of formula (ID) where X is bromine to form the compound of formula (IE). This reaction can be carried out at ambient, sub-ambient or super-ambient temperature conditions suitably in a dark or yellow light conditions to ensure that the diazirine group is not affected. Generally, the reaction temperature can range from about −20° C. to 120° C.

Scheme 2

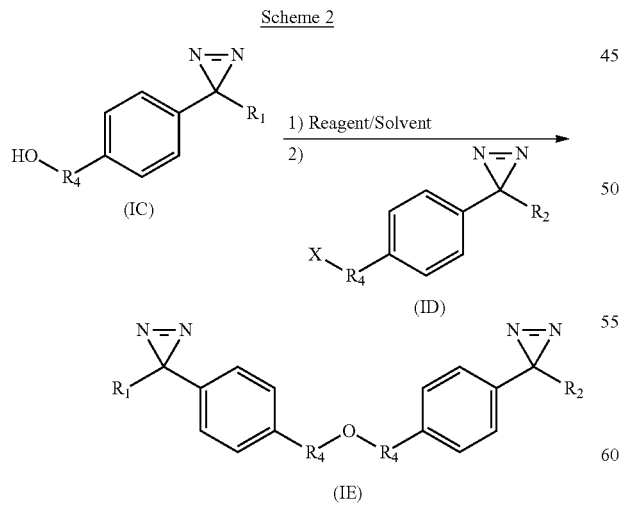

In a similar manner various other compounds of formula (I) or (II) can be prepared employing appropriate starting materials and reagents, as one of skill in the art of organic chemistry can appreciate.

As described herein, the compounds of this invention, particularly, the compounds of formula (I) and (II) are highly effective as carbene precursors when exposed to suitable radiation, and are therefore useful as photo crosslinking agents as further described in detail hereinbelow and illustrated by specific examples hereafter.

Photoimageable Compositions

In another aspect of this invention there is also provided a photoimageable composition comprising:

a polymer capable of reacting with a carbene to form a carbene inserted product;

a compound of the formula (I) or (II):

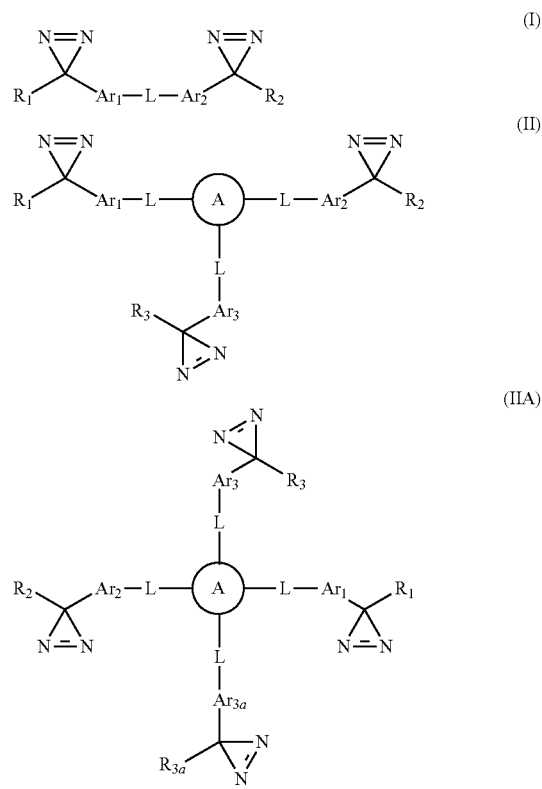

wherein,

A is a carbon, silicon, oxygen or nitrogen central core moiety;

L is a bond or a divalent linking or a spacer group selected from:

—C(O)O—R$_4$—OC(O)—, —C(O)O—R$_4$—, —R$_4$—OC(O)—R$_4$—, —C(O)—R$_4$—OC(O)—, —C(O)—R$_4$—, —R$_4$—C(O)—R$_4$—, —O—R$_4$—OC(O)—, —O—R$_4$—O—, —O—R$_4$—, —R$_4$—O—R$_4$—, —C(O)NR$_5$—R$_4$—OC(O)—, —C(O)NR$_5$—R$_4$—NR$_5$C(O)—, —C(O)NR$_5$—R$_4$—, —R$_4$—NR$_5$C(O)—R$_4$—, —C(O)—R$_4$—NR$_5$C(O)—, —NR$_5$—R$_4$—OC(O)—, —NR$_5$—R$_4$—NR$_5$C(O)—, —NR$_5$—R$_4$—, —R$_4$—NR$_5$—R$_4$—, —NR$_5$—R$_4$—NR$_5$—, —R$_4$—, and

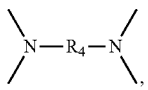

where each occurrence of $R_4$ may be the same or different which is a divalent group independently selected from $(C_1-C_{12})$alkyl, $(C_3-C_{12})$cycloalkyl, $(C_6-C_{12})$aryl, $(C_6-C_{12})$aryl$(C_1-C_{12})$alkyl, $(C_6-C_{10})$heteroaryl, $(C_6-C_{10})$heteroaryl$(C_1-C_{12})$alkyl, $-(CH_2-CH_2-O)_a-$, where a is an integer from 1 to 10, provided that when $R_4$ is $-(CH_2-CH_2-O)_a-$ then the oxygen end of said group is linked only with either carbon or silicon containing linking group, which are optionally substituted with a group selected from halogen, $-OH$, $(C_1-C_4)$alkyl, $(C_1-C_4)$alkoxy, $(C_6-C_{10})$aryl, $(C_6-C_{10})$aryloxy, $(C_6-C_{12})$aralkyl and $(C_6-C_{12})$aralkyloxy; and $R_5$ is hydrogen, $(C_1-C_6)$alkyl, $(C_6-C_{10})$aryl or $(C_6-C_{10})$aralkyl;

$R_1$, $R_2$, $R_3$ and $R_{3a}$ are the same or different and each is independently selected from $(C_1-C_{12})$alkyl, where portions of hydrogen on alkyl are replaced with fluorine, $(C_1-C_{12})$perfluoroalkyl, $(C_6-C_{12})$aryl, $(C_6-C_{12})$aryl$(C_1-C_{12})$alkyl, where portions of hydrogen on alkyl are replaced with fluorine, and $(C_6-C_{12})$arylperfluoro$(C_1-C_{12})$alkyl; and $Ar_1$, $Ar_2$, $Ar_3$ and $Ar_{3a}$ are the same or different and each is independently selected from $(C_6-C_{12})$arylene or $(C_6-C_{12})$heteroarylene group optionally substituted with a group selected from halogen, $-OH$, $(C_1-C_4)$alkyl, $(C_1-C_4)$alkoxy, $(C_6-C_{10})$aryl, $(C_6-C_{12})$aryloxy, $(C_6-C_{12})$aryl$(C_1-C_4)$alkyl and $(C_6-C_{12})$aryl$(C_1-C_4)$alkyloxy; and a carrier solvent.

It should be noted that in this aspect of the invention, any one or more of the diazirine compounds of formula (I) or (II) as described herein can be employed without any limitation. It should further be noted that any one or more of the polymers that is capable of reacting with a carbene formed from the diazirine compounds of formula (I) or (II) can be used to form the photoimageable compositions of this invention. That is, a photoimageable composition containing one or more compounds of formula (I) or (II) is exposed to suitable radiation, the compounds of formula (I) or (II) will then form a highly active carbene, which can readily insert into OH, NH, CH or olefinic group or any other functional group that may be present in the polymer which allows such insertion of carbene to form the corresponding carbene insertion product, thus causing crosslinking because of the fact that the compounds of formula (I) or (II) have at least two diazirine functional groups. Since the compositions of this invention always cause crosslinking upon exposure to radiation, the exposed regions are crosslinked and thus become less soluble upon exposure, and as a result facilitate forming images when imagewise exposed using a photopatternable mask. Accordingly, the compositions of this invention can be used as "negative tone" compositions to form photolithographic images.

It should also be noted that a variety of other known "carbene precursors" can also be used in combination with one or more compounds of formula (I) or (II) of this invention. Various such carbene precursors are known in the art and are specifically disclosed in U.S. Pat. No. 8,530,212, pertinent portions of which are incorporated herein by reference. Briefly, such carbene precursors include diazo compounds and their precursors, hydrazones. A variety of diazo- or hydrazone compounds can be used in combination with the photoimageable compositions of this invention.

In one of the embodiments the compositions of this invention encompasses a polymer which is capable of forming a cross-linked product upon reaction with a carbene. Any of the polymers that is capable of reacting with a carbene generated from the compounds of formula (I) or (II) can be used in the compositions of this invention. Representative examples of such polymers include natural or synthetic polymers including without any limitation a polysaccharide, a polyglycoside, a cellulose, a polypeptide, a protein, a polyester, a polyether, an epoxy resin, a polyacrylate, a polyacrylic, a polymethacrylate, a polycarbonate, a polyketone, polyetheretherketone (PEEK), a polyacetal, a polyamide, a polyetherimide, a polyimide, a polysulfone, a polyolefin, a polystyrenic, a polyvinyl and its copolymer, poly(vinyl chloride) (PVC), a polysilane, a polysiloxane, a polyurea, a polyurethane, polylactic acid, polyvinylidene chloride, a fluoro-polymer, a polyethylene imine or a salt thereof.

In yet another embodiment the polymer that can be employed to form the photoimageable composition is selected from the group consisting of:

a polycycloolefinic polymer;

a polyacrylate;

polyvinyl butyral, commercially available as BUTACITE® (from DuPont), MOWITAL® (from Kuraray) or BUTVAR® (from Eastman Chemical);

polyvinyl trimethylsilane (PVTMS);

hydrogenated styrenic block copolymer (commercially available as SEPTON® 2002 from Kuraray);

ethyl cellulose; and poly(4-tert-butyl-styrene).

In another embodiment the polymer employed is a polycycloolefinic polymer. A variety of cyclo olefinic polymers are commercially available and all of which can be used in the compositions of this invention. For example, ZEONEX® (from Nippon Zeon) and TOPAS® (from Topas Advanced Materials Inc.) can be used to form the compositions of this invention.

In another embodiment, the compositions of this invention encompasses a polymer which is a polycycloolefinic polymer comprising at least one repeat unit represented by formula (IIIA), said repeat unit is derived from a monomer of formula (III):

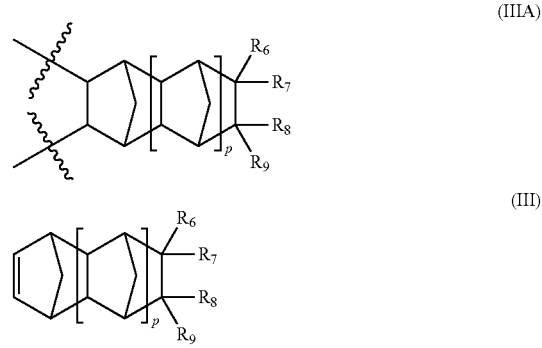

wherein:

∿ denotes a place of bonding with another repeat unit;

p is an integer 0, 1 or 2;

$R_6$, $R_7$, $R_8$ and $R_9$ are the same or different and each independently of one another is selected from hydrogen, linear or branched $(C_1-C_{16})$alkyl, $(C_1-C_{16})$alkenyl, hydroxy$(C_1-C_{16})$alkyl, perfluoro$(C_1-C_{12})$alkyl, $(C_3-$ $C_{12}$)cycloalkyl, $(C_6-C_{12})$bicycloalkyl, $(C_7-C_{14})$tricycloalkyl, $(C_6-C_{10})$aryl, $(C_6-C_{10})$aryl$(C_1-C_3)$alkyl, perfluoro$(C_6-C_{10})$aryl, perfluoro$(C_6-C_{10})$aryl$(C_1-C_3)$alkyl, di$(C_1-C_2)$alkylmaleimide$(C_3-C_6)$alkyl, di$(C_1-C_2)$alkylmaleimide$(C_2-C_6)$alkoxy$(C_1-C_2)$alkyl, hydroxy, $(C_1-C_{12})$alkoxy, $(C_3-C_{12})$cycloalkoxy, $(C_6-C_{12})$bicycloalkoxy, $(C_7-C_{14})$tricycloalkoxy, $(C_1-C_{12})$alkoxy$(C_1-C_8)$alkyl, $(C_6-C_{10})$aryloxy$(C_1-C_3)$alkyl, $(C_5-C_{10})$heteroaryloxy$(C_1-C_3)$alkyl, $(C_6-C_{10})$aryloxy, $(C_5-C_{10})$heteroaryloxy, $(C_1-C_6)$acyloxy, $(C_1-C_6)$acyloxy, oxiranyl$(C_0-C_8)$alkyl, oxiranyl$(CH_2)_cO(CH_2)_d$—, halogen or a group of formula (A):

$$-(CH_2)_c-(OCH_2-CH_2)_d-OR \quad (A)$$

wherein:

c is an integer 0, 1, 2, 3 or 4;

d is an integer 0, 1, 2, 3 or 4; and

R is linear or branched $(C_1-C_6)$alkyl, $(C_5-C_8)$cycloalkyl, $(C_6-C_{10})$aryl or $(C_7-C_{12})$aralkyl; where each of the aforementioned substituents are optionally substituted with a group selected from halogen or hydroxy.

In another embodiment of this invention the polymer employed in the composition of this invention is a cycloolefinic polymer, wherein the polymer comprises two or more different repeat units of formula (IIIA). That is the polymer employed is either a copolymer or a terpolymer.

It should further be noted that any of the known monomers of formula (III) can be employed in this aspect of the invention. Representative examples of monomers of formula (IV) include the following without any limitations:

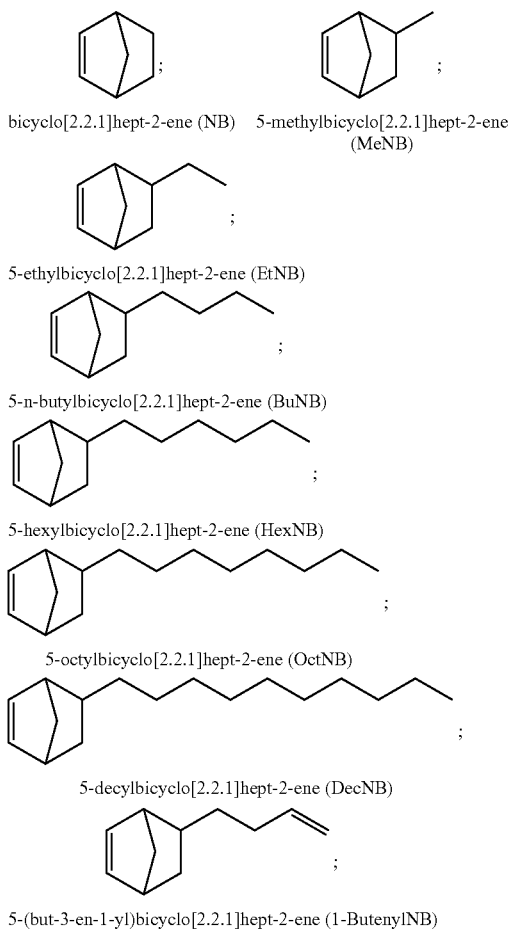

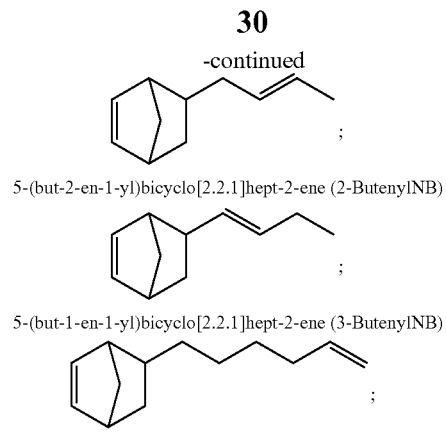

5-(but-2-en-1-yl)bicyclo[2.2.1]hept-2-ene (2-ButenylNB)

5-(but-1-en-1-yl)bicyclo[2.2.1]hept-2-ene (3-ButenylNB)

5-(hex-5-en-1-yl)bicyclo[2.2.1]hept-2-ene (HexenylNB)

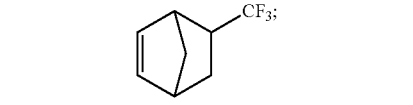

5-trifluoromethylbicyclo[2.2.1]hept-2-ene (CF$_3$NB)

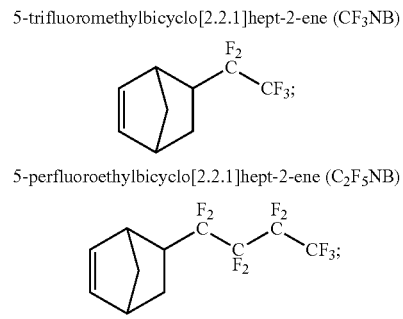

5-perfluoroethylbicyclo[2.2.1]hept-2-ene (C$_2$F$_5$NB)

5-n-perfluorobutylbicyclo[2.2.1]hept-2-ene (C$_4$F$_9$NB)

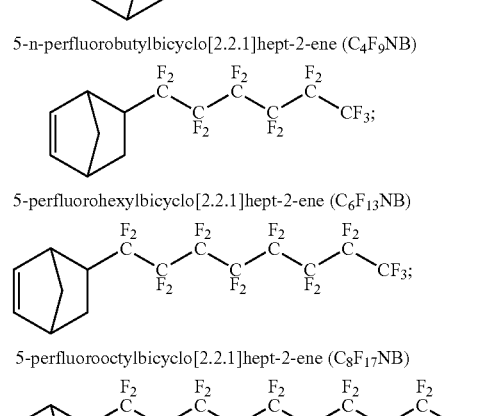

5-perfluorohexylbicyclo[2.2.1]hept-2-ene (C$_6$F$_{13}$NB)

5-perfluorooctylbicyclo[2.2.1]hept-2-ene (C$_8$F$_{17}$NB)

5-perfluorodecylbicyclo[2.2.1]hept-2-ene (C$_{10}$F$_{21}$NB)

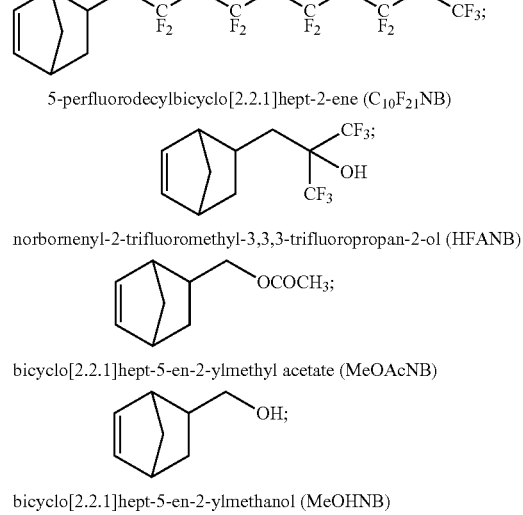

norbornenyl-2-trifluoromethyl-3,3,3-trifluoropropan-2-ol (HFANB)

bicyclo[2.2.1]hept-5-en-2-ylmethyl acetate (MeOAcNB)

bicyclo[2.2.1]hept-5-en-2-ylmethanol (MeOHNB)

5-((2-(2-methoxyethoxy)ethoxy)methyl)bicyclo[2.2.1]hept-2-ene
(NBTON)

1-(bicyclo[2.2.1]hept-5-en-2-yl)-2,5,8,11-tetraoxadodecane
(NBTODD)

5-(2-(2-ethoxyethoxy)ethyl)bicyclo[2.2.1]hept-2-ene 5-(2-(2-(2-propoxyethoxy)ethoxy)ethoxy)bicyclo[2.2.1]hept-2-ene 3-(bicyclo[2.2.1]hept-5-en-2-yl)propanoic acid (NBEtCOOH)

ethyl 3-(bicyclo[2.2.1]hept-5-en-2-yl)propanoate (EPEsNB)

1-(bicyclo[2.2.1]hept-5-en-2-ylmethyl)-3,4-dimethyl-1H-pyrrole-2,5-dione
(MeDMMINB)

1-(3-(bicyclo[2.2.1]hept-5-en-2-yl)propyl-3,4-dimethyl-1H-pyrrole-2,5-dione (PrDMMINB)

1-(4-(bicyclo[2.2.1]hept-5-en-2-yl)butyl)-3,4-dimethyl-1H-pyrrole-2,5-dione (BuDMMINB)

1-(6-(bicyclo[2.2.1]hept-5-en-2-yl)hexyl)-3,4-dimethyl-1H-pyrrole-2,5-dione (HexDMMINB)

2-((bicyclo[2.2.1]hept-5-en-2-ylmethoxy)methyl)oxirane (MGENB)

2-(bicyclo[2.2.1]hept-5-en-2-yl)oxirane 2-(7-(bicyclo[2.2.1]hept-5-en-2-yl)hepthyl)oxirane 5-phenethylbicyclo[2.2.1]hept-2-ene (PENB)

2-(bicyclo[2.2.1]hept-5-en-2-yl)bicyclo[2.2.1]heptane (also referred to herein as NBNBA)

and 2-(bicyclo[2.2.1]hept-5-en-2-yl)-5-phenyl-bicyclo[2.2.1]heptane (also referred to herein as NBNBAPh)

bicyclo[2.2.1]hept-5-en-2-yl(ethoxy)dimethylsilane (NBSiMe$_2$(OEt))

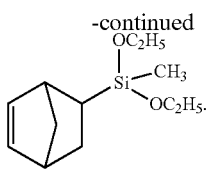

bicyclo[2.2.1]hept-5-en-2-yl(triethoxy)silane (TESNB)

Again, any of the polymerizable monomer as described herein can be used. For example, the polymerizable monomer is selected from the group consisting of:
bicyclo[2.2.1]hept-2-ene (NB);
5-butylbicyclo[2.2.1]hept-2-ene (BuNB);
5-hexylbicyclo[2.2.1]hept-2-ene (HexNB);
5-octylbicyclo[2.2.1]hept-2-ene (OctNB);
5-decylbicyclo[2.2.1]hept-2-ene (DecNB);
5-(but-3-en-1-yl)bicyclo[2.2.1]hept-2-ene (1-ButenylNB);
5-(but-2-en-1-yl)bicyclo[2.2.1]hept-2-ene (2-ButenylNB);
5-(but-1-en-1-yl)bicyclo[2.2.1]hept-2-ene (3-ButenylNB);
5-perfluoroethylbicyclo[2.2.1]hept-2-ene ($C_2F_5$NB);
5-n-perfluorobutylbicyclo[2.2.1]hept-2-ene ($C_4F_9$NB);
5-perfluorohexylbicyclo[2.2.1]hept-2-ene ($C_6F_{13}$NB);
norbornenyl-2-trifluoromethyl-3,3,3-trifluoropropan-2-ol (HFANB);
1-(3-(bicyclo[2.2.1]hept-5-en-2-yl)propyl)-3,4-dimethyl-1H-pyrrole-2,5-dione (PrDMMINB);
1-(4-(bicyclo[2.2.1]hept-5-en-2-yl)butyl)-3,4-dimethyl-1H-pyrrole-2,5-dione (BuDMMINB);
1-(6-(bicyclo[2.2.1]hept-5-en-2-yl)hexyl)-3,4-dimethyl-1H-pyrrole-2,5-dione (HexDMMINB);
5-phenethylbicyclo[2.2.1]hept-2-ene (PENB);
5-((2-(2-methoxyethoxy)ethoxy)methyl)bicyclo[2.2.1]hept-2-ene (NBTON);
bicyclo[2.2.1]hept-5-en-2-yl(ethoxy)dimethylsilane (NBSiMe$_2$(OEt);
bicyclo[2.2.1]hept-5-en-2-ylmethyl acetate (MeOAcNB); and
bicyclo[2.2.1]hept-5-en-2-ylmethanol (MeOHNB).

The polymers derived from monomer of formula (III) can generally be made by a variety of procedures known in the art. For example, by employing a transition metal catalysts, such as palladium or nickel catalyst, the polymers can be formed by way of vinyl addition polymerization procedures, see U.S. Pat. No. 7,799,883, pertinent portions of which is incorporated herein by reference.

In a further embodiment, the composition of this invention encompasses a polymer which is a copolymer of maleic anhydride and at least one repeat unit of formula (IIIA). Such copolymers are generally made by a free radical polymerization conditions.

In yet a further embodiment, the composition of this invention encompasses a copolymer of maleic anhydride and a monomer of formula (IIIA) wherein the maleic anhydride ring of the copolymer is at least partially opened with an alcohol, see for example U.S. Pat. No. 8,715,900, pertinent portions of which are incorporated herein by reference. In another embodiment the compositions of this invention encompasses a copolymer of maleic anhydride and a monomer of formula (IIIA) wherein the maleic anhydride ring of the copolymer is at least partially opened with an amine.

Non-limiting examples of such copolymer include:
a copolymer containing repeating units derived from bicyclo[2.2.1]hept-2-ene and maleic anhydride ring opened with n-butanol; and a copolymer containing repeating units derived from 5-n-perfluorobutylbicyclo[2.2.1]hept-2-ene and maleic anhydride ring opened with n-butanol.

Various other non-limiting examples of polymers that are suitable for forming the compositions of this invention may be selected from the group consisting of:
poly(5-hexylbicyclo[2.2.1]hept-2-ene) (poly(HexNB));
poly(5-(but-3-en-1-yl)bicyclo[2.2.1]hept-2-ene) (poly(1-ButenylNB));
poly(5-n-perfluorobutylbicyclo[2.2.1]hept-2-ene) (poly($C_4F_9$NB));
a copolymer of bicyclo[2.2.1]hept-2-ene (NB) and bicyclo[2.2.1]hept-5-en-2-yl(ethoxy)dimethylsilane (NBSiMe$_2$(OEt);
a copolymer of norbornenyl-2-trifluoromethyl-3,3,3-trifluoropropan-2-ol (HFANB) and bicyclo[2.2.1]hept-5-en-2-ylmethanol (MeOHNB); and
a copolymer containing repeating units derived from bicyclo[2.2.1]hept-2-ene and maleic anhydride ring opened with n-butanol.

The polymers employed to form the compositions of this invention generally exhibit a number average molecular weight ($M_w$) of at least about 3,000. In another embodiment, the polymer employed in the composition of this invention has a $M_w$ of at least about 10,000. In yet another embodiment, the polymer employed in the composition of this invention has a $M_w$ of at least about 50,000. In some other embodiments, the polymer of this invention has a $M_w$ of at least about 100,000. In some other embodiments, the polymer of this invention has a $M_w$ ranging from about 100,000 to 500,000. The weight average molecular weight ($M_w$) of the polymer can be determined by any of the known techniques, such as for example, by gel permeation chromatography (GPC) equipped with suitable detector and calibration standards, such as differential refractive index detector calibrated with narrow-distribution polystyrene standards.

As already noted above, the composition of this invention encompasses one or more compounds of formula (I) or (II). As further noted any of the compounds as enumerated herein without any limitation can be used in forming the compositions of this invention.

Any of the solvents that can dissolve all of the components of the composition of this invention can be used as a carrier solvent. Representative examples of such solvents include alcohols, such as ethanol, isopropanol, butanols, and the like. Ketone solvents, such as acetone, methyl ethyl ketone (MEK), cyclohexanone, cyclopentanone, and the like. Hydrocarbon solvents, such as decane, toluene, p-menthane, and the like. Ester solvents, such as benzyl acetate, ethyl acetate, and the like. Glycol and ether solvents, such as diethylene glycol dimethyl ether, propylene glycol monomethyl ether (PGME), propylene glycol monomethyl ether acetate (PGMEA), and the like. Various other solvents, such as N-methyl-2-pyrrolidone (NMP), gamma-butyrolactone (GBL), N,N-dimethylacetamide, N,N-dimethylformamide (DMF), anisole, methyl 3-methoxypropionate, tetrahydrofuran (THF), 3-ethoxy-1,1,1,2,3,4,4,5,5,6,6,6-dodecafluoro-2-(trifluoromethyl)hexane (HFE-7500), 1,1,1,2,2,3,3,4,4-nonafluoro-4-methoxybutane, 1,1,1,2,2,3,4,4,4-nonafluoro-3-methoxybutane and mixtures in any combination thereof.

In another aspect of this invention there is further provided a method of forming a film for the fabrication of a microelectronic or optoelectronic device comprising:
coating a suitable substrate with a composition according to this invention to form a film;
patterning the film with a mask by exposing to a suitable radiation;

developing the film after exposure to form a photopattern; and curing the film by heating to a suitable temperature.

The coating of the desired substrate to form a film with photosensitive composition of this invention can be performed by any of the coating procedures as described herein and/or known to one skilled in the art, such as by spin coating. Other suitable coating methods include without any limitation spraying, doctor blading, meniscus coating, ink jet coating and slot coating. Suitable substrate includes any appropriate substrate as is, or may be used for electrical, electronic or optoelectronic devices, for example, a semiconductor substrate, a ceramic substrate, a glass substrate.

Next, the coated substrate is first softbaked before the curing, i.e., heated to facilitate the removal of residual casting solvent, for example to a temperature from 60° C. to 120° C. for from about 1 to 30 minutes, although other appropriate temperatures and times can be used. In some embodiments the substrate is first softbaked before the curing at a temperature of from about 70° C. to about 100° C. for 2 minutes to 10 minutes. After the heating, the film is generally imagewise exposed to an appropriate wavelength of actinic radiation, wavelength is generally selected based on the choice of the diazirine compound of formula (I) or (II) employed in the polymer composition as described herein. However, generally such appropriate wavelength is that produced by a mercury vapor lamp which is from 200 to 450 nm depending upon the type of mercury vapor lamp employed. It will be understood that the phrase "imagewise exposure" means exposing through a masking element to provide for a resulting pattern of exposed and unexposed portion of the film.

After an imagewise exposure of the film formed from the composition in accordance with the present invention, a development process is employed. As noted above, the compositions of this invention function primarily as "negative tone" compositions, that is, the development process removes only unexposed portions of the film thus leaving a negative image of the masking layer in the film.

Suitable developers can include aqueous solutions of inorganic alkalis such as sodium hydroxide, potassium hydroxide, sodium carbonate; ammonia, or aqueous solutions of organic bases such as 0.26 N tetramethylammonium hydroxide (TMAH), ethylamine, triethylamine and triethanolamine. Aqueous solutions of TMAH are well known developer solutions in the semiconductor industry. Suitable developers can also include organic solvents such as PGMEA, 2-heptanone, cyclohexanone, toluene, xylene, ethyl benzene, mesitylene and butyl acetate, among others, or mixtures of these solvents in any combination thereof.

Thus some embodiments of the present invention provide self-imageable films that after imagewise exposure, a resulting image is developed using an aqueous base solution, while for other such embodiments a resulting image is developed using an organic solvent. Regardless of which type of developer is employed, after the image is developed, the substrate is rinsed to remove excess developer solution, typical rinse agents are water or appropriate alcohols and mixtures thereof.

Accordingly, in some embodiments the developer employed is an aqueous developer which is tetramethylammonium hydroxide (TMAH). In some other embodiments the developer employed is an organic solvent which is selected from the group consisting of decane, p-menthane, 3-ethoxy-1,1,1,2,3,4,4,5,5,6,6,6-dodecafluoro-2-(trifluoromethyl)hexane (HFE-7500), and mixtures in any combination thereof.

After the aforementioned rinsing, the substrate is dried and the imaged film finally cured. That is to say, the image is fixed. Such reaction is generally a further cross-linking reaction that can be initiated by heating and/or non-imagewise blanket exposure of the remaining material. Such exposure and heating can be in separate steps or combined as is found appropriate for the specific use of the imaged film. The blanket exposure is generally performed using the same energy source as employed in the imagewise exposure although any appropriate energy source can be employed. The heating is generally carried out at a desirable temperature, for example, from above 110° C. for a time of from several minutes to one or more hours. Where the remaining layer has been exposed during the imagewise exposure, image fixing is generally accomplished by a heating step to be tailored to complete any reaction initiated by the exposure. However an additional blanket exposure and heating, as discussed above, can also be employed. It should be realized, however, that the choice of a final cure process is also a function of the type of device being formed; thus a final fixing of the image may not be a final cure where the remaining layer is to be used as an adhesive layer or structure.

Accordingly, in some embodiments the resulting imagewise film or layer is cured by heating the patterned and developed substrate at a temperature of from about 120° C. to about 250° C. for about 20 minutes to about 240 minutes. In some other embodiments such curing is carried out at a temperature of from about 130° C. to about 200° C. for about 30 minutes to about 180 minutes. In yet some other embodiments such curing is carried out at a temperature of from about 150° C. to about 180° C. for about 60 minutes to about 120 minutes. Finally, in some other embodiments of this invention, the curing is performed at a temperature of from about 130° C. to about 200° C. at an incremental heating ramp of about 5° C./minute and for about 1 to 3 hours.

The devices are produced by using embodiments of the alkali soluble photosensitive resin composition of the present invention to form layers which are characterized as having high heat resistance, an appropriate water absorption rate, high transparency, and low permittivity. In addition, such layers generally have an advantageous coefficient of elasticity after curing.

As previously mentioned, exemplary applications for embodiments of the photosensitive compositions in accordance with the present invention include redistribution layer, die attach adhesive, wafer bonding adhesive, insulation films (interlayer dielectric layers), protecting films (passivation layers), mechanical buffer films (stress buffer layers) or flattening films for a variety of semiconductor devices, printed wiring boards. Specific applications of such embodiments encompass a die-attach adhesive to form a single or multilayer semiconductor device, dielectric film which is formed on a semiconductor device; a buffer coat film which is formed on the passivation film; an interlayer insulation film which is formed over a circuit formed on a semiconductor device.

Advantageously, it has now been found that the photosensitive compositions of this invention may be useful to form adhesive layers for bonding the semiconductor chips to each other, such as in chip-stack applications. For example, a redistribution layer used for such a purpose is composed of a cured product of the photosensitive adhesive composition of the present invention. Surprisingly, it has now been found that although the adhesive layer is a single-layer structure, it not only exhibits sufficient adhesiveness to the substrate but also is free of significant stress resulting due to the curing step. Accordingly, it may now be possible to avoid undesirably thick layer of film encompassing the chip as a laminate. It has been further observed that the laminates formed in accordance with the present invention are reliable in that the relaxation of stress concentration between layers caused by thermal expansion difference or the like can be obtained. As a result, the semiconductor device having low height and high reliability can be obtained. That is, devices with low aspect ratio and low thickness can be obtained. Such semiconductor device becomes particularly advantageous to electronic equipment, which has very small internal volume and is in use while carrying as a mobile device, for example. Even more advantageously, by practice of this invention it may now be possible to form a variety of electronic devices featuring hitherto unachievable level of miniaturization, thinning and light-weight, and the function of the semiconductor device is not easily damaged even if such devices are subject to rugged operations such as swinging or dropping.

Accordingly, in some of the embodiments of this invention there is also provided a cured product obtained by curing the photosensitive composition as described herein. In another embodiment there is also provided an optoelectronic or microelectronic device comprising the cured product of this invention as described herein.

Advantageously it has also been found that the composition of this invention features low dielectric constant, generally less than 3.9, as described herein. Accordingly, in some of the embodiments the cured product obtained from the composition of this invention exhibits a dielectric constant of 3.6 or less at 1 MHz. In some other embodiments the cured product obtained from the composition of this invention exhibits a dielectric constant of 3.2 or less at 1 MHz. In yet some other embodiments the cured product obtained from the composition of this invention exhibits a dielectric constant of 3.0 or less at 1 MHz.

The following examples are detailed descriptions of methods of preparation and use of certain compounds/monomers, polymers and compositions of the present invention. The detailed preparations fall within the scope of, and serve to exemplify, the more generally described methods of preparation set forth above. The examples are presented for illustrative purposes only, and are not intended as a restriction on the scope of the invention. As used in the examples and throughout the specification the ratio of monomer to catalyst is based on a mole to mole basis.

This invention is further illustrated by the following examples which are provided for illustration purposes and in no way limit the scope of the present invention.

EXAMPLES

The following abbreviations have been used hereinbefore and hereafter in describing some of the compounds, instruments and/or methods employed to illustrate certain of the embodiments of this invention:
NB: bicyclo[2.2.1]hept-2-ene; 1-ButenylNB: 5-(but-3-en-1-yl)bicyclo[2.2.1]hept-2-ene; NBSiMe$_2$(OEt): bicyclo[2.2.1]hept-5-en-2-yl(ethoxy)dimethylsilane; MeOAcNB: bicyclo[2.2.1]hept-5-en-2-ylmethyl acetate; MeOHNB: bicyclo[2.2.1]hept-5-en-2-ylmethanol; HFANB: norbornenyl-2-trifluoromethyl-3,3,3-trifluoropropan-2-ol; HexNB: 5-hexylbicyclo-[2.2.1]hept-2-ene; C$_4$F$_9$NB: 5-perfluorobutylbicyclo[2.2.1]hept-2-ene; EPEsNB: ethyl 3-(bicyclo[2.2.1]hept-5-en-2-yl)propanoate; NBEtCOOH: 3-(bicyclo[2.2.1]hept-5-en-2-yl)propanoic acid; MA: maleic anhydride; NBTON: 5-((2-(2-methoxyethoxy)ethoxy)methyl)bicyclo[2.2.1]hept-2-ene; d-IBU: diisobutylene; ROMA: ring opened maleic anhydride copolymer with alcohol; ROME ring opened maleic anhydride copolymer with amine; PGME: propylene glycol methyl ether; PGMEA: propylene glycol methyl ether acetate; EtOAc: ethyl acetate; HFE-7500: 3-ethoxy-1,1,1,2,3,4,4,5,5,6,6,6-dodecafluoro-2-(trifluoromethyl)hexane; NaH: sodium hydride; DANFABA: N,N-dimethylaniliniumtetrakis(pentafluorophenyl)-borate; LiFABA: lithium (diethyl ether) tetrakis(pentafluorophenyl)borate ([Li(OEt$_2$)$_{2.5}$][B(C$_6$F$_5$)$_4$]); R.T.—room temperature; LC-MS: liquid chromatography-mass spectroscopy; GPC: gel permeation chromatography; phr: parts per hundred parts of resin.

The following examples describe the procedures used for the preparation of various compounds as disclosed herein including certain of the starting materials employed in the preparation of the compounds of this invention. However, it should be noted that these examples are intended to illustrate the disclosure without limiting the scope thereof.

Example 1

Propane-1,3-diyl bis(4-(3-(trifluoromethyl)-3H-diazirin-3-yl)benzoate)

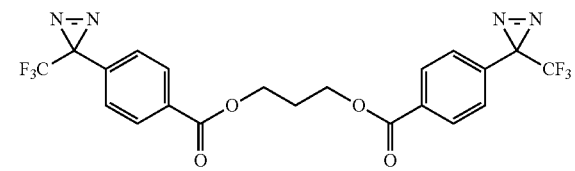 [SMILES: O=C(OCCCOC(=O)c1ccc(C2(C(F)(F)F)N=N2)cc1)c1ccc(C2(C(F)(F)F)N=N2)cc1]

All of the procedures described herein were carried out under yellow light conditions. To a 60 mL crimp cap bottle equipped with a stirbar was added 4-[3-(trifluoromethyl)-3H-diazirin-3-yl]benzoic acid (2 g, 8.7 mmol, 2.5 equiv., purchased from TCI America), followed by potassium carbonate (2.4 g, 17.3 mmol, 5 equiv.) and acetone (20 mL). To the stirring slurry was added diiodopropane (1.1 g, 3.5 mmol, 1 equiv.). The reaction mixture was allowed to stir for 20 h.

The reaction mixture was then filtered through #4 filter paper followed by dilution with EtOAc (20 mL). The resulting solution was washed with water (3×10 mL). The organic layer was concentrated to a very small volume (0.73 g, 42% recovery). LC-MS analysis of the reaction mixture indicated formation of two products: the target compound (M+1−2N$_2$=445) and the mono-iodo byproduct, 3-iodopropyl 4-(3-(trifluoromethyl)-3H-diazirin-3-yl)benzoate, (M+1−N$_2$=371) in a 1:3 ratio based on area percent using a UV detector at 254 nm. The mixture was used without further purification.

Example 2

3,3'-((oxybis(methylene))bis(4,1-phenylene))bis(3-(trifluoromethyl)-3H-diazirine)

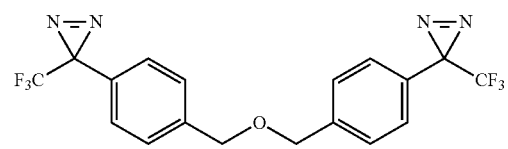 [SMILES: FC(F)(F)C1(c2ccc(COCc3ccc(C4(C(F)(F)F)N=N4)cc3)cc2)N=N1]

All of the procedures described herein were carried out in the dark. To a 60 mL crimp cap bottle equipped with a magnetic stirbar was added NaH (60% dispersion in mineral oil) (0.204 g, 5.1 mmol, 1.1 eq). The bottle was sealed with a septum cap and a vent needle (20 gauge) was added. THF (7 mL) was syringed into the reactor. The solution of 4-[3-(trifluoromethyl)-3H-diazirin-3-yl]benzyl alcohol (1 g, 4.6 mmol, purchased from TCI America) in THF (3 mL) was added slowly to the reactor by syringe (bubbling was visible). This mixture stirred for 10 min followed by addition of neat 4-[3-(trifluoromethyl)-3H-diazirin-3-yl]benzyl bromide (1.3 g, 4.6 mmol, purchased from TCI America) by syringe. The reaction mixture was allowed to stir at room temperature overnight (20 h).

Water (10 mL) was then added to the reaction slurry resulting in a biphasic mixture. The organic layer was removed from the aqueous layer and washed with water (2×10 mL). The organic layer was concentrated under vacuum to afford the crude product as a yellow oil/solid mixture. The crude material was placed onto a column of silica gel (3 cm×26 cm) and 25 mL fractions were taken eluting with 10% EtOAc in hexane. Fractions 3 and 4 were combined and concentrated to afford the title compound as a yellow oil (1 g). LC-MS showed that the final product was 77% pure (M−2$N_2$=358) based on area percent using a 254 nm detector. $^1$H NMR (tetrachloroethane-$d_2$): 7.45 (d, 4H), 7.25 (d, 4H), 4.61 (s, 2H). $^{13}$C NMR (tetrachloroethane-$d_2$): 140.02, 128.65, 127.98, 122.25 (q), 71.64, 71.44.

B. Polymer Synthesis Examples

Polymer Examples

Various polymers as described herein for forming the photoimageable compositions of this invention were commercially available and were used as such. The vinyl addition polymers containing the functionalized norbornene monomers can also be made in accordance with procedures known in the art. A few of the representative non-limiting examples of such polymers are also described hereinbelow.

Example 3

Poly(HexNB)

HexNB (1.6 Kg, 9 moles), cyclohexane (6.2 Kg) and ethyl acetate (3 Kg) were mixed together, nitrogen sparged for 30 minutes and cooled to 20° C. ($\eta^6$-toluene)Ni($C_6F_5$)$_2$ (12.2 g, 0.025 moles) and toluene (250 g) were added to the monomer mixture. The reactor temperature was increased to 40° C. and the mixture was stirred for 3 hours. Residual catalyst was removed and the polymer was precipitated into isopropanol. After isolating the polymer by filtration, it was dried in a vacuum oven at 80° C. The polymer was characterized by GPC: $M_w$: 190,000 $M_n$: 75,000

Example 4

Copolymer of NB/NBSiMe$_2$(OEt) (82/18)

Norbornene (60.2 g, 0.64 moles), NBSiMe$_2$(OEt) (31.4 g, 0.16 moles), cyclohexane (546 g) and ethyl acetate (223 g) were mixed together, nitrogen sparged for 30 minutes and heated to 35° C. ($\eta^6$-toluene)Ni($C_6F_5$)$_2$ (5.54 g, 0.011 moles) and ethyl acetate (50 g) were added to the monomer mixture. The reactor temperature was increased to 40° C. and the mixture was stirred for 2 hours. Residual catalyst was removed and the polymer was precipitated into methanol. After isolating the polymer by filtration, it was dried in a vacuum oven at 50° C. The polymer was characterized by GPC and $^1$H NMR: $M_w$: 89,000 $M_n$: 49,000; composition as determined by $^1$H NMR was: 82% norbornene/18% NBSiMe$_2$(OEt)

Example 5

Copolymer of HFANB/MeOHNB (63/37)

A reactor was charged with HFANB (1.81 Kg, 6.6 moles), MeOAcNB (728 g, 4.4 moles), DANFABA (28.8 g, 0.04 moles), formic acid (27.5 g, 0.6 moles), and toluene (2000 g). A syringe pump was charged with additional MeOAcNB (200 g, 1.2 moles). In a dry box the palladium catalyst, palladium(acetylacetonato)(acetonitrile)$_2$ tetrakis(pentafluorophenyl)borate [Pd(acac)($CH_3CN$)$_2$]B($C_6F_5$)$_4$, (11.6 g) was charged to a pressure cylinder. Anhydrous ethyl acetate (132 g) was added to the pressure cylinder. The solution in the reactor was heated to 70° C. under a nitrogen atmosphere. The catalyst solution was transferred to the heated reaction mixture. Following catalyst injection the syringe pump containing MeOAcNB was started and monomer was added to the reactor according to a predetermined schedule: 0.733 g/min for 28 minutes, 0.262 g/min for 78 minutes, 0.190 g/min for 108 minutes, 0.159 g/min for 128 minutes, 0.134 g/min for 153 minutes, 0.106 g/min for 194 minutes, 0.078 g/min for 264 minutes and 0.068 g/min for 303 minutes. At the end of the predetermined schedule any residual MeOAcNB monomer in the syringe was discarded. The solution was mixed for 22 hours following catalyst injection. The polymer solution was cooled to room temperature. Residual catalyst was removed and the acetoxy group of the repeat units of MeOAcNB was removed by hydrolysis to form MeOHNB repeat units in the polymer backbone. The polymer solution was precipitated into heptanes and dried in a vacuum oven at 70° C. The polymer was characterized by GPC and $^1$H NMR: $M_w$: 3640 $M_n$: 2640; composition as determined by $^1$H NMR was: 63% HFANB/37% MeOHNB.

Example 6 poly(ButentylNB)

A solution of LiFABA, ([Li($Et_2O$)$_{2.5}$][B($C_6F_5$)$_4$], (47.4 mg, 0.054 mmol) and butenylnorbornene (20 g, 136 mmol) in toluene (total solution volume 50 mL) was heated to 70° C. Then a solution of [(allyl)palladium (trinaphthylphosphine)(trifluoroacetate)] (9.6 mg, 0.014 mmol, 0.01 M) in toluene was added to the reaction mixture. The reaction mixture stirred for 1 h at 70° C. The reaction mixture was allowed to cool to room temperature. The reaction mixture was diluted to 100 mL total volume with THF and was poured into MeOH (~10 fold excess). The precipitated polymer was filtered, then dried in a vacuum oven at 50° C. overnight to give a white powder. Yield: 18 g, 90%. The polymer was characterized by GPC and $^1$H NMR: $M_w$: 24,800, $M_w/M_n$: 2.25. The ratio of terminal to isomerized olefins associated with the butenyl pendent group was determined by $^1$H NMR methods and were found to be 25 to 1.

Example 7

Poly(NBC$_4$F$_9$)

NBC$_4$F$_9$ (62.4 g, 0.2 moles), trifluorotoluene (52.4 g) and toluene (15 g) were mixed together, nitrogen sparged for 30 minutes and heated to 25° C. (η6-toluene)Ni(C$_6$F$_5$)$_2$ (0.97 g, 0.002 moles) and toluene (7.9 g) were added to the monomer mixture. The mixture was stirred for 8 hours. Residual catalyst was removed and the polymer was precipitated into methanol. After isolating the polymer by filtration, it was dried in a vacuum oven at 75° C. The polymer was characterized by GPC: M$_w$: 210,000 M$_n$: 150,000.

Example 8

Ring Opened Copolymer of NB/MA with n-BuOH ROMA

Maleic Anhydride (MA, 122.4 g, 1.25 mol), 2-norbornene (NB, 117.6 g, 1.25 mol) and dimethyl 2,2'-azobis(2-methylpropionate) (11.5 g, 50 mmol) were dissolved in MEK (150.8 g) and toluene (77.7 g) and charged to an appropriately sized reaction vessel. The solution was sparged with nitrogen for 10 min to remove oxygen and then heated to 60° C. with stirring. After 16 hr, MEK (320 g) was added to the reaction mixture. The resulting solution was added to a suspension of NaOH (12.5 g, 0.31 mol), n-BuOH (463.1 g, 6.25 mol) and mixed at 45° C. for 3 hr. The mixture was then cooled to 40° C., treated with 88% formic acid (49 g, 0.94 mol) for protonation, and then washed with water three times. The organic phase was separated and residual monomer extracted with hexane. After the extraction, PGMEA was added to the reaction mixture and heated to 120° C. for additional reaction. Samples were removed to monitor the dissolution rate of the polymer and the reaction mixture cooled and solvent exchanged into PGMEA when the desired dissolution rate was achieved (~800 nm/sec in 0.26 N TMAH). The ring-opened polymer as a 20 wt % solution was obtained (1107.7 g). The polymer was characterized by GPC: M$_w$: 13,700, M$_n$: 7,400). The polymer solution was heated to 120° C. in a stainless steel reactor. Aliquots of the reaction mixture were taken over time and the dissolution rate of this polymer in 0.26 N TMAH was determined (see Table 1). After 5 hours the desired dissolution rate was achieved and the reactor was cooled. The solution was concentrated by rotoevaporation until a solids content of ~21% was reached. The polymer was characterized by GPC: M$_w$: 11,600, M$_n$: 5,630.

TABLE 1

| Reaction time (hours) | Dissolution rate (nm/sec) |
|---|---|
| 0 | 705 |
| 2 | 380 |
| 4 | 298 |
| 5 | 213 |

Example 8A

Ring Opened Copolymer of NB/MA with n-BuOH ROMA

Example 8 was substantially repeated in this Example 8a to obtain a polymer having M$_w$ of 11,600.

Example 8B

Copolymer of HFANB/NBEtCOOH (75/25)

A reactor was charged with HFANB (4.9 kg, 17 moles), EPEsNB (0.58 kg, 3.1 moles), toluene (18.4 kg) and DME (2.4 kg). A pressure cylinder was charged with additional EPEsNB (0.58 kg, 3.1 moles) and toluene (2.6 kg). In a dry box (η$^6$-toluene)Ni(C$_6$F$_5$)$_2$ (116 g) was charged to a pressure cylinder. Anhydrous toluene (1 kg) was airlessly added to the pressure cylinder. The solution in the reactor was sparged with nitrogen for 15 minutes and then heated to 50° C. The (η$^6$-toluene)Ni(C$_6$F$_5$)$_2$ solution was transferred to the heated reaction mixture at a rate of 194 g/min for 15 minutes. At the end of the predetermined schedule any residual EPEsNB/toluene mixture in the pressure cylinder was discarded. The solution was mixed for 22 hours following catalyst injection. The polymer solution was cooled to room temperature. Residual catalyst was removed and the EPEsNB was deprotected to obtain the title polymer. The polymer solution was solvent exchanged into PGME and characterized by GPC: M$_w$ 130,000 M$_n$ 54,000.

Example 8C d-IBU/NBTON/MA Terpolymer Ring Opened with n-Octyl Amine (ROMI Polymer)

d-IBU/NBTON/MA polymer (192 g) was dissolved in PGMEA (356 g) to obtain 35% (w/w) solution. Part of this polymer solution (250 g) was transferred to a 0.5 L glass reactor equipped with a mechanical stirrer, nitrogen inlet and a port connected to a syringe pump. The solution was sparged with nitrogen and kept under a 20 psig nitrogen blanket and heated to 50° C. while stirring. A solution of 1-octylamine (30 g) was made in PGMEA (30 g) and transferred to a stainless-steel syringe. 55 mL of this amine solution (46.4 g) was added to the polymer solution in the reactor at 0.5 mL/min rate using a syringe pump. After amine addition was complete the reaction mixture was heated to 90° C. for 4 hours while stirring. The resulting amine treated polymer was withdrawn from the reactor after allowing it to cool to 25° C. The resulting polymer was characterized by GPC: M$_w$ of 26,600 (PDI 1.8). The acid number of the product was 118 mg KOH/g.

Small aliquot (5 g) of the product was added to n-heptane (40 g) while stirring to separate the solid polymer by precipitation. The solid obtained was washed with n-heptane (20 g) and dried at 80° C. for 24 hours in a vacuum oven to obtain 2 g of the solid polymer (100% isolated yield). The FT-IR analysis of the solid indicated the presence of carboxylic acid group (broad peak at 2000-3500 cm$^{-1}$).

Example 8D

Poly(DecNB)

DecNB (290 g, 1.2 moles), cyclohexane (1.1 Kg) and anhydrous ethyl acetate (0.53 Kg) were mixed together, nitrogen sparged for 30 minutes and cooled to 20° C. (η$^6$-toluene)Ni(C$_6$F$_5$)$_2$ (1.9 g, 0.004 moles) and anhydrous ethyl acetate (17 g) were added to the monomer mixture. The reactor temperature was increased to 40° C. and the mixture was stirred for 2 hours. Residual catalyst was removed and the polymer was precipitated into isopropanol. After isolating the polymer by filtration, it was dried in a vacuum oven at 80° C. M$_w$: 170,000 M$_n$: 94,000

Photoimageable Polymer Composition and Imaging Studies

The following Examples illustrate the photocrosslinking and imageability of the compounds of this invention with a variety of polymers as described herein.

Example 9

Formulation and Imaging of Polymer of Example 6 Using Bis(diazirine) of Example 1

Polymer from Example 1, poly(butenylNB), (1 g) and bis(diazirine) of Example 1 (0.73 g) were dissolved in 9 g decane/benzyl acetate (90/10) by rolling the mixture overnight. The solution (3 g) was then dispensed onto a 4 inch thermal oxide silicon wafer. The wafer was spun at 300 rpm for 40 sec and post apply baked at 120° C. for 2 min. The film thickness was determined using a Dektak profilometer and was found to be 0.7 μm.

The film on the silicon wafer was image-wise exposed through a 365 nm band pass filter using an ABM mask aligner and at exposure dose of 967 mJ/cm². The film was developed using decane as the solvent for 10 seconds. The quality of the resulting 3D relief images were determined by inspection of the wafer under a microscope. The contact hole resolution was determined to be 10 μm.

Examples 10-24

Formulation and Imaging of Various Polymers Using Bis(diazirine) of Example 2

In each of Examples 10-24, the polymer compositions were prepared as set forth below.

In Example 10, polymer from Example 3, poly(HexNB), (0.55 g) and bis(diazirine) of Example 2 (0.11 g) were dissolved in 5 g decane after rolling overnight. This solution (2.5 g was further diluted with a 2.5 g of a 10% solution of polymer of Example 3 in decane to give a 10% solution of polymer of Example 3 with 10 phr bis(diazirine) of Example 2 (10 parts per hundred parts of the polymer of Example 3).

In Example 11, bis(diazirine) of Example 2 (0.1 g) was added to a 10% solution of ZEONEX® 480R (available from Nippon Zeon) in p-menthane (10 g). The resulting mixture was rolled overnight.

In Example 12, a 10% solution of TOPAS® 6013S-04 (available from Topas Advanced Polymers) in p-menthane and 10 phr bis(diazirine) of Example 2 was prepared.

In Example 13, bis(diazirine) of Example 2 (0.1 g) was added to a solution of the polymer from Example 4, copolymer of NB/NBSiMe$_2$(OEt), (1 g) in p-menthane (9 g).

In Example 14, poly(4-t-butyl)styrene (available from Monomer Polymer and Dajac Labs, 1 g) was dissolved in 4 g of p-menthane. To this solution was added 0.1 g of bis(diazirine) of Example 2.

In Example 15, bis(diazirine) of Example 2 (0.1 g) was added to a solution of the polymer of Example 5, copolymer of HFANB/MeOHNB, in isopropanol (0.92 g of polymer in 5 g of isopropanol).

In Example 16, 0.33 g of a solution of polymer from Example 7, poly(NBC$_4$F$_9$), (1 g in 8 g of HFE-7500) was diluted with 2.64 g of HFE-7500. This solution was mixed with a solution 0.1 g of bis(diazirine) of Example 2 in 0.9 g of HFE-7500.

In Example 17, bis(diazirine) of Example 2 (0.34 g) was added to the polymer solution from Example 8 (5 g, approximately 1 g of polymer of Example 8 in 4 g of PGMEA).

Similarly, Examples 18 to Examples 24 were prepared using the solvents as follows: Example 18 in PGMEA, Example 19 in PGMEA, Example 20 in CPN, Examples 21 and 22 in PGMEA, Example 23 in IPA and Example 24 in decane.

In each of the Examples 10-24, the solution (3 g) was filtered through a 0.2 μm PTFE syringe filter onto a 4 inch thermal oxide silicon wafer.

In each of the Examples 10-24, the solution (3 g) dispensed onto a 4 inch thermal oxide silicon wafer was spun at 500 rpm for 40 sec then post apply baked at 80° C. for 2 min. The film thickness was determined using a Dektak profilometer, the film thickness, FT in μm is summarized in Table 2 for each of these Examples.

In each of the Examples 10-24, the film on the silicon wafer thus formed was then image-wise exposed through a 365 nm band pass filter using an ABM mask aligner. The exposure dose used in each of these Examples are different depending upon the nature of the polymer employed to obtain desirable resolution of the images formed, and are summarized in Table 2.

It is evident from the data presented in Table 2, the degree of crosslinking with the polymer and the diazirine of this invention results in the observed image resolution. That is, higher the crosslinking between the polymer and diazirine, higher the image resolution. The film was developed using various solvents as summarized in Table 2.

TABLE 2

| Example No. | Polymer Example No. | $M_w$ | Solvent | FT | Exp. Dose (mJ/cm²) | Develop Conditions | CH resol | FT loss (%) |
|---|---|---|---|---|---|---|---|---|
| 10 | Example 3 | 190,000 | D | 1.18 | 255 | 30 sec D | 7 μm | 7.6 |
| 11 | Zeonex 480 | 133,000* | PM | 1.36 | 967 | 30 sec PM | 10 μm | 12 |
| 12 | Topas 6013S-04 | 205,000* | PM | 1.31 | 967 | 20 sec PM | 15 μm | 1.5 |
| 13 | Example 4 | 89,000 | PM | 2.06 | 644 | 30 sec PM/D | 10 μm | 7.6 |
| 14 | p(4-t-Bu-styrene) | 105,000 | PM | 1.62 | 967 | 20 sec PM | 40 μm | 40 |
| 15 | Example 5 | 3,640 | IPA | 2.23 | 644 | 120 sec TMAH | 20 μm | 0 |
| 16 | Example 7 | 210,000 | HFE-7500 | 1.75 | 791 | 10 sec HFE-7500 | 80 μm | 29 |
| 17 | Example 8 | 13,700 | PGMEA | 0.88 | 967 | 10 sec TMAH | 10 μm | 27 |
| 18 | Example 8a | 11,600 | PGMEA | 0.82 HMDS | 405 | 2 + 2 sec TMAH | 5 μm | 30 |
| 19 | Example 8b | 130,000 | PGMEA | 1.84 HMDS | 255 | 2 + 2 sec TMAH | 10 μm | 5 |

TABLE 2-continued

| Example No. | Polymer Example No. | $M_w$ | Solvent | FT | Exp. Dose (mJ/cm$^2$) | Develop Conditions | CH resol | FT loss (%) |
|---|---|---|---|---|---|---|---|---|
| 20 | Poly(isobutyl-methacrylate) | | CPN | 1.81 | 405 | 10 + 10 sec TMAH | 10 μm | 16 |
| 21 | Example 8c | 26,600 | PGMEA | 0.7 | 510 | 2 sec TMAH | 7 μm | 28 |
| 22 | Example 8c | 26,600 | PGMEA | 0.7 | 967 | 2 sec TMAH | 15 μm | 0 |
| 23 | Example 5 | 3,640 | IPA | 0.44 | 113 | 60 sec TMAH | 5 μm | 16 |
| 24 | Example 8d | 169,000 | D | 1 | 510 | 3 × 10 sec D | 7 μm | 3 |

*GPC in cyclohexane;
FT = film thickness;
Exp. dose = exposure dose at 365 nm;
D = decane;
PM = p-menthane;
IPA = isopropanol;
HFE-7500: 3-ethoxy-1,1,1,2,3,4,4,5,5,6,6,6-dodecafluoro-2-(trifluoromethyl)hexane;
PGMEA: propylene glycol methyl ether acetate;
HMDS: hexamethyldisilane;
CPN: cyclopentane;
TMAH = 0.26N aqueous tetramethyl ammonium hydroxide.
CH resol = contact hole resolution.

As further summarized in Table 2, the time needed to develop the images depended on the type of polymer employed. The quality of the resulting 3D relief images were determined by inspection of the wafer under a microscope.

Figure 2:
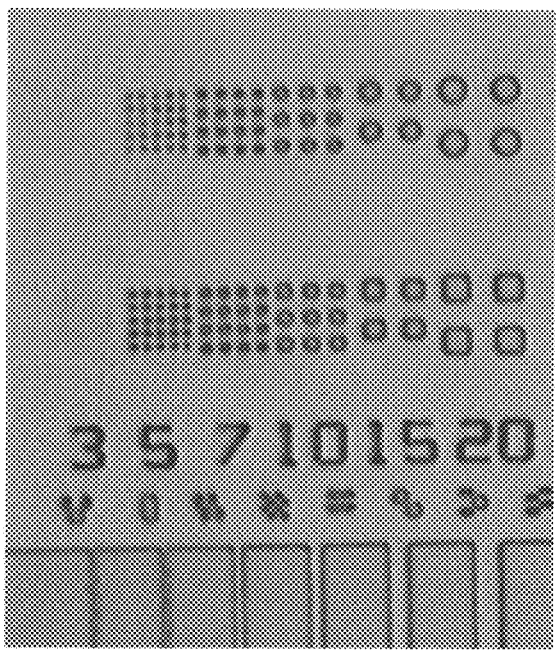
FIG. 2 is a lithographic image obtained for the composition of this invention containing the polymer, ZEONEX® 480R (a commercially available cyclo olefin polymer from Zeon Corporation, Tokyo, Japan) and the diazirine as set forth in Example 2.
Figure 3:
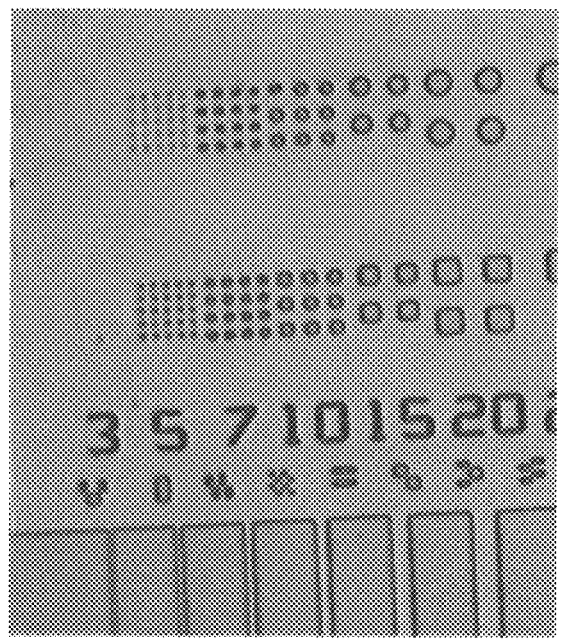
FIG. 3 is a lithographic image obtained for the composition of this invention containing the polymer, TOPAS® 6013S-04 (a commercially available cyclo olefin polymer from Topas Advanced Polymers, Inc., Florence, Ky., USA) and the diazirine as set forth in Example 2.
Figure 4:
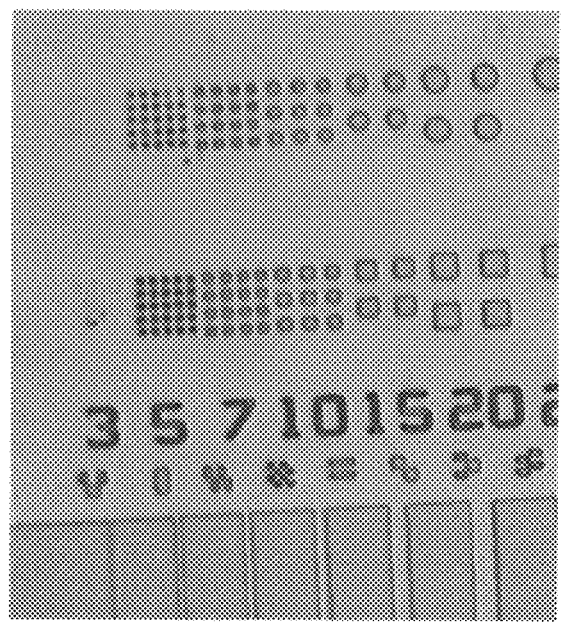
FIG. 4 is a lithographic image obtained for the composition of this invention containing the NB/NBSiMe$_2$(OEt) copolymer as set forth in Example 4 and the diazirine as set forth in Example 2.

Now turning to FIG. 1, which shows a photolithograph of the developed silicon wafer from Example 10, which clearly shows that the bis(diazirine) compounds of this invention are very effective in forming the crosslinked polymers as apparent from the image resolution of the contact holes at 7 μm. Similarly, the FIGS. 2 to 4 show photolithographs of various other polymer compositions formed from the diazirines of this invention, all of which show similar image resolutions.

COMPARATIVE EXAMPLES

The following Comparative Examples 1 and 2 are provided to show the bis(diazirines) of this invention exhibit superior properties when compared with similar photocrosslinking agents reported in the literature. For example, it has been reported that certain of the azide compounds upon photo exposure provides a nitrene intermediate which can be used as a crosslinking agent. Comparative Example 1 shows that use of such bis-diazide compound failed to provide similar photocrosslinking effect as demonstrated by the bis(diazirine) compounds of this invention. The bis-azide compound, (2E,6E)-2,6-bis(4-azidobenzylidene)-4-ethylcyclohexanone was used in Comparative Example 1, which is also known as BAC-E of the formula:

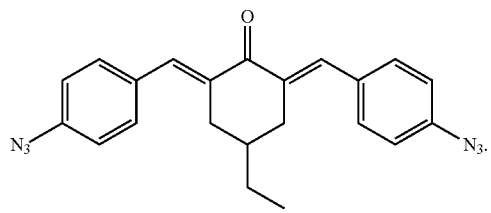

BAC-E

Comparative Example 1

Formulation and Imaging of Polymer of Example 3 with BAC-E

The polymer of Example 3, poly(hexylNB), (1.29 g) was dissolved in 11.65 g of decane. To this solution was added 0.065 g of BAC-E in 1.3 g toluene. 5.0 g of this formulation was diluted with 4.5 g decane and 0.5 g of toluene.

The solution (3 g) was filtered through a 0.45 μm PTFE syringe filter onto a 4 inch thermal oxide silicon wafer. The wafer was spun at 300 rpm for 40 sec then post apply baked at 120° C. for 2 min. The film thickness was determined using a Dektak profilometer and was found to be 0.5 μm.

The film on the silicon wafer was image-wise exposed through a 365 nm band pass filter using an ABM mask aligner at an exposure dose of 1000 mJ/cm$^2$. The exposed film was developed in decane for 15 seconds. The quality of the resulting 3D relief images were determined by inspection of the wafer under a microscope, no images were observed as the entire film had dissolved during develop, thus demonstrating that no photocrosslinking took place under these conditions.

Comparative Example 2

Imaging of Polymer of Example 6 without Additives

The polymer from Example 6, poly(butenylNB), (1 g) was dissolved in 9 g decane:benzyl acetate (90:10). The solution (3 g) was deposited onto a 4 inch thermal oxide silicon wafer. The wafer was spun at 300 rpm for 40 sec then post apply baked at 120° C. for 2 min. The film on the silicon wafer was image-wise exposed through a 365 nm band pass filter at an exposure dose of 967 mJ/cm$^2$ using an ABM mask aligner. The film was developed 10 sec with decane at 50 rpm with 1000 rpm ramp then spun dry at 2000 rpm for 30 sec. The film completely dissolved after development.

Comparative Example 2 again demonstrates that an active photocrosslinking agent is needed to obtain crosslinked polymer upon exposure to suitable radiation.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of the formula (IA), (II) or (IIA):

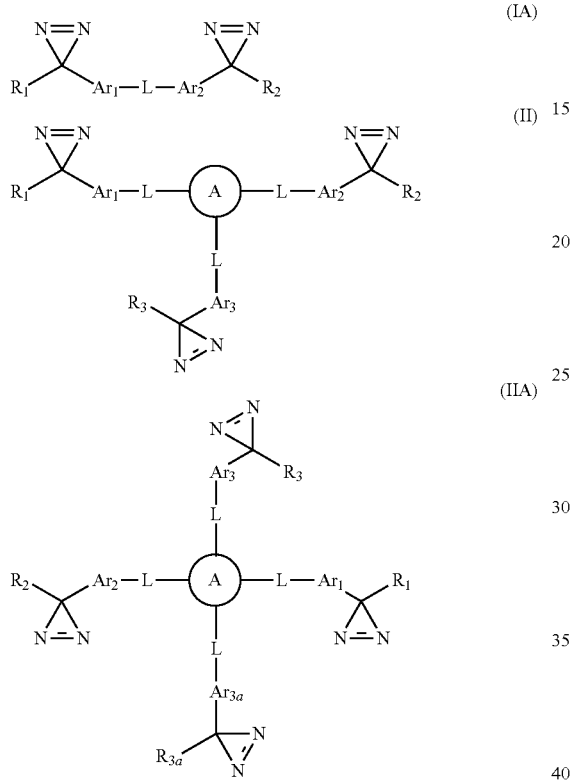

wherein,

A is a carbon, silicon, oxygen or nitrogen central core moiety;

L is a bond or a divalent linking or a spacer group selected from:
—C(O)O—$R_4$—OC(O)—, —C(O)O—$R_4$—, —$R_4$—OC(O)—$R_4$—, —C(O)—$R_4$—OC(O)—, —C(O)—$R_4$—, —$R_4$—C(O)—$R_4$—, —O—$R_4$—OC(O)—, —O—$R_4$—O—, —O—$R_4$—, —$R_4$—O—$R_4$—, —C(O)NR$_5$—$R_4$—OC(O)—, —C(O)NR$_5$—$R_4$—NR$_5$C(O)—, —C(O)NR$_5$—$R_4$—, —$R_4$—NR$_5$C(O)—$R_4$—, —C(O)—$R_4$—NR$_5$C(O)—, —NR$_5$—$R_4$—OC(O)—, —NR$_5$—$R_4$—NR$_5$C(O)—, —NR$_5$—$R_4$—, —$R_4$—NR$_5$—$R_4$—, —NR$_5$—$R_4$—NR$_5$—, —$R_4$—, and

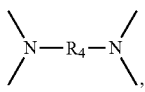

where each occurrence of $R_4$ may be the same or different which is a divalent group independently selected from $(C_1-C_{12})$alkyl, $(C_3-C_{12})$cycloalkyl, $(C_6-C_{12})$aryl, $(C_6-C_{12})$aryl$(C_1-C_{12})$alkyl, $(C_6-C_{10})$heteroaryl, $(C_6-C_{10})$heteroaryl $(C_1-C_{12})$alkyl, —(CH$_2$—CH$_2$—O)$_a$—, where a is an integer from 1 to 10, provided that when $R_4$ is —(CH$_2$—CH$_2$—O)$_a$— then the oxygen end of said group is linked only with either carbon or silicon containing linking group, which are optionally substituted with a group selected from halogen, —OH, $(C_1-C_4)$alkyl, $(C_1-C_4)$alkoxy, $(C_6-C_{10})$aryl, $(C_6-C_{10})$aryloxy, $(C_6-C_{12})$aralkyl and $(C_6-C_{12})$aralkyloxy; and $R_5$ is hydrogen, $(C_1-C_6)$alkyl, $(C_6-C_{10})$aryl or $(C_6-C_{10})$aralkyl;

$R_1$, $R_2$, $R_3$ and $R_{3a}$ are the same or different and each is independently selected from $(C_1-C_{12})$alkyl, where portions of hydrogen on alkyl are replaced with fluorine, $(C_1-C_{12})$perfluoroalkyl, $(C_6-C_{12})$aryl, $(C_6-C_{12})$aryl$(C_1-C_{12})$alkyl, where portions of hydrogen on alkyl are replaced with fluorine, and $(C_6-C_{12})$arylperfluoro$(C_1-C_{12})$alkyl; and $Ar_1$, $Ar_2$, $Ar_3$ and $Ar_{3a}$ are the same or different and each is independently selected from $(C_6-C_{12})$arylene or $(C_6-C_{12})$heteroarylene group optionally substituted with a group selected from halogen, —OH, $(C_1-C_4)$alkyl, $(C_1-C_4)$alkoxy, $(C_6-C_{10})$aryl, $(C_6-C_{12})$aryloxy, $(C_6-C_{12})$aryl$(C_1-C_4)$alkyl and $(C_6-C_{12})$aryl$(C_1-C_4)$alkyloxy; and with the proviso that the following compounds are excluded:

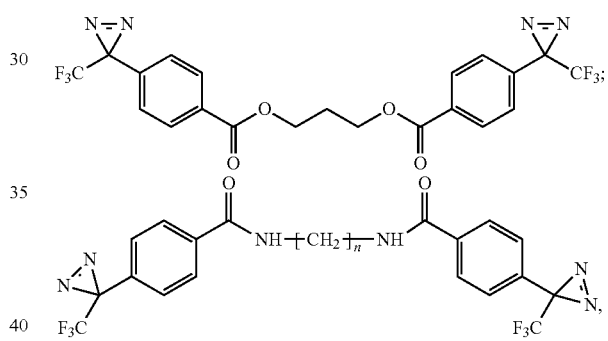

where n is 7 or 12; and

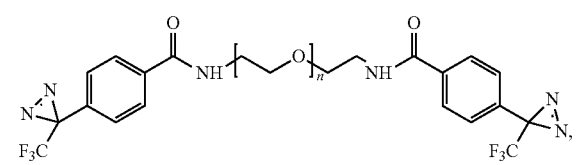

where n is 3 or 5.

2. A compound of the formula (IA):

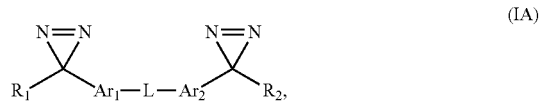

wherein:

L is a linking group selected from:
—C(O)O—(CH$_2$)$_b$—O(CO)—, —C(O)O—(CH$_2$)$_b$—, —(CH$_2$)$_b$—O(CO)—(CH$_2$)$_b$—, —C(O)—(CH$_2$)$_b$—O(CO)—, —C(O)—(CH$_2$)$_b$—, —(CH$_2$)$_b$—(CO)—(CH$_2$)$_b$—, —O—(CH$_2$)$_b$—O(CO)—, —O—

—(CH$_2$)$_b$—O—, —O—(CH$_2$)$_b$—, —(CH$_2$)$_b$—O—(CH$_2$)$_b$—, —C(O)NR$_5$—(CH$_2$)$_b$—O(CO)—, —C(O)NR$_5$—(CH$_2$)$_b$—NR$_5$(CO)—, —C(O)NR$_5$—(CH$_2$)$_b$—, —(CH$_2$)$_b$—NR$_5$(CO)—(CH$_2$)$_b$—, —C(O)—(CH$_2$)$_b$—NR$_5$(CO)—, —NR$_5$—(CH$_2$)$_b$—O(CO)—, —NR$_5$—(CH$_2$)$_b$—NR$_5$(CO)—, —NR$_5$—(CH$_2$)$_b$—, —(CH$_2$)$_b$—NR$_5$—(CH$_2$)$_b$—, —NR$_5$—(CH$_2$)$_b$—NR$_5$— where b is an integer from 1 to 12; R$_5$ is hydrogen, (C$_1$-C$_4$)alkyl, phenyl, naphthyl, tolyl or benzyl;

R$_1$ and R$_2$ are the same or different and each independently selected from (C$_1$-C$_6$)alkyl, (C$_1$-C$_6$)perfluoroalkyl, (C$_6$-C$_8$)aryl, (C$_6$-C$_8$)perfluoroaryl, (C$_6$-C$_{10}$)aralkyl or (C$_6$-C$_{10}$)perfluoroarylperfluoroalkyl; and Ar$_1$ and Ar$_2$ are the same or different and are independently of each other selected from phenylene or naphthalene group optionally substituted with a group selected from halogen, —OH, (C$_1$-C$_4$)alkyl, (C$_1$-C$_4$)alkoxy, (C$_6$-C$_{10}$)aryl, (C$_6$-C$_{10}$)aryloxy, (C$_6$-C$_{12}$)aralkyl and (C$_6$-C$_{12}$)aralkyloxy; and with the proviso that the following compounds are excluded:

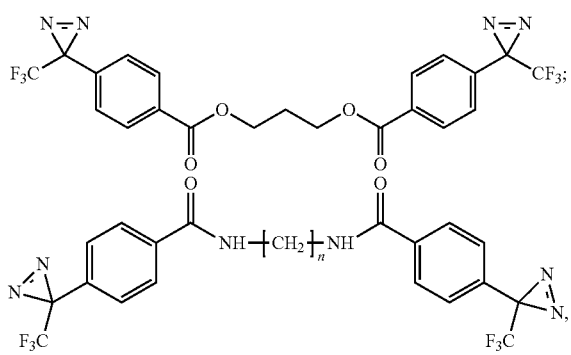

where n is 7 or 12; and

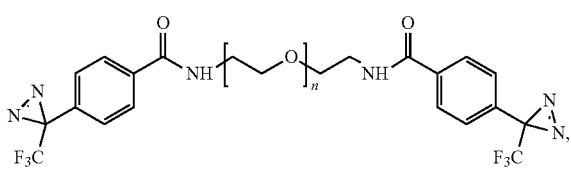

where n is 3 or 5.

3. The compound according to claim 2, wherein:
L is a linking group selected from:
—C(O)O—(CH$_2$)$_b$—O(CO)—, —C(O)O—(CH$_2$)$_b$—, —(CH$_2$)$_b$—O(CO)—(CH$_2$)$_b$—, —O—(CH$_2$)$_b$—O—, —O—(CH$_2$)$_b$—OH, —(CH$_2$)$_b$—O—(CH$_2$)$_b$—, —C(O)NR$_5$—(CH$_2$)$_b$—NR$_5$(CO)—, —NR$_5$—(CH$_2$)$_b$—, —(CH$_2$)$_b$—NR$_5$—(CH$_2$)$_b$—, —NR$_5$—(CH$_2$)$_b$—NR$_5$— where b is an integer from 1 to 6; R$_5$ is hydrogen, methyl, ethyl, propyl, isopropyl, n-butyl, tert-butyl, phenyl, naphthyl, tolyl or benzyl;

R$_1$ and R$_2$ are the same or different and each independently selected from methyl, ethyl, propyl, isopropyl, n-butyl, tert-butyl, trifluoromethyl, pentafluoroethyl, heptafluoropropyl, phenyl, pentafluorophenyl, benzyl or heptafluorobenzyl; and Ar$_1$ and Ar$_2$ are the same or different and are independently of each other selected from phenylene or naphthalene group optionally substituted with a group selected from fluorine, methyl, ethyl, propyl, isopropyl, n-butyl, tert-butyl, methoxy, ethoxy, propoxy, isopropoxy, n-butoxy, tert-butoxy, phenyl, naphthyl, tolyl, benzyl, phenoxy, naphthyloxy, tolyloxy or benzyloxy.

4. The compound according to claim 1, which is selected from the group consisting of:
methylene bis(4-(3-(trifluoromethyl)-3H-diazirin-3-yl)benzoate);
ethane-1,2-diyl bis(4-(3-(trifluoromethyl)-3H-diazirin-3-yl)benzoate);
butane-1,4-diyl bis(4-(3-(trifluoromethyl)-3H-diazirin-3-yl)benzoate);
3,3'-((oxybis(methylene))bis(4,1-phenylene))bis(3-(trifluoromethyl)-3H-diazirine);
3,3'-((oxybis(ethane-2,1-diyl))bis(4,1-phenylene))bis(3-(trifluoromethyl)-3H-diazirine);
3-(trifluoromethyl)-3-(4-(3-((4-(3-(trifluoromethyl)-3H-diazirin-3-yl)benzyl)oxy)propyl)phenyl)-3H-diazirine;
3-(trifluoromethyl)-3-(4-(2-((4-(3-(trifluoromethyl)-3H-diazirin-3-yl)benzyl)oxy)ethyl)phenyl)-3H-diazirine;
4-(3-(trifluoromethyl)-3H-diazirin-3-yl)benzyl 4-(3-(trifluoromethyl)-3H-diazirin-3-yl)benzoate;
4-(3-(trifluoromethyl)-3H-diazirin-3-yl)phenethyl 2-(4-(3-(trifluoromethyl)-3H-diazirin-3-yl)phenyl)acetate;
2-oxo-2-(4-(3-(trifluoromethyl)-3H-diazirin-3-yl)phenyl)ethyl 3-(3-(trifluoromethyl)-3H-diazirin-3-yl)benzoate;
1,3-bis(4-(3-(trifluoromethyl)-3H-diazirin-3-yl)phenyl)propan-1-one;
1,3-bis(4-(3-(trifluoromethyl)-3H-diazirin-3-yl)phenyl)propan-2-one;
(4-(3-(trifluoromethyl)-3H-diazirin-3-yl)phenoxy)methyl 3-(3-(trifluoromethyl)-3H-diazirin-3-yl)benzoate;
1,2-bis(4-(3-(trifluoromethyl)-3H-diazirin-3-yl)phenoxy)ethane;
3-(trifluoromethyl)-3-(4-(3-(4-(3-(trifluoromethyl)-3H-diazirin-3-yl)phenoxy)propyl)phenyl)-3H-diazirine;
(N-methyl-4-(3-(trifluoromethyl)-3H-diazirin-3-yl)benzamido)methyl 4-(3-(trifluoromethyl)-3H-diazirin-3-yl)benzoate;
N,N'-methylenebis(N-methyl-4-(3-(trifluoromethyl)-3H-diazirin-3-yl)benzamide);
2-ethyl-2-(((4-(3-(trifluoromethyl)-3H-diazirin-3-yl)benzoyl)oxy)methyl)propane-1,3-diyl bis(4-(3-(trifluoromethyl)-3H-diazirin-3-yl)benzoate);
2-(perfluoroethyl)-2-(((4-(3-(trifluoromethyl)-3H-diazirin-3-yl)benzoyl)oxy)methyl)propane-1,3-diyl bis(4-(3-(trifluoromethyl)-3H-diazirin-3-yl)benzoate);
3,3'-((((2-ethyl-2-(((4-(3-(trifluoromethyl)-3H-diazirin-3-yl)benzyl)oxy)methyl)propane-1,3-diyl)bis(oxy))bis(methylene))bis(4,1-phenylene))bis(3-(trifluoromethyl)-3H-diazirine); and
3,3'-((((2-(perfluoroethyl)-2-(((4-(3-(trifluoromethyl)-3H-diazirin-3-yl)benzyl)oxy)methyl)propane-1,3-diyl)bis(oxy))bis(methylene))bis(4,1-phenylene))bis(3-(trifluoromethyl)-3H-diazirine).

5. A photoimageable composition comprising:
a polymer capable of reacting with a carbene to form a carbene inserted product;
a compound of the formula (IA), (II) or (IIA):

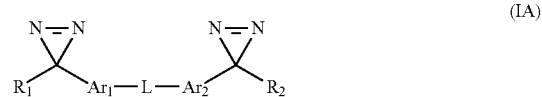

(IA)

-continued

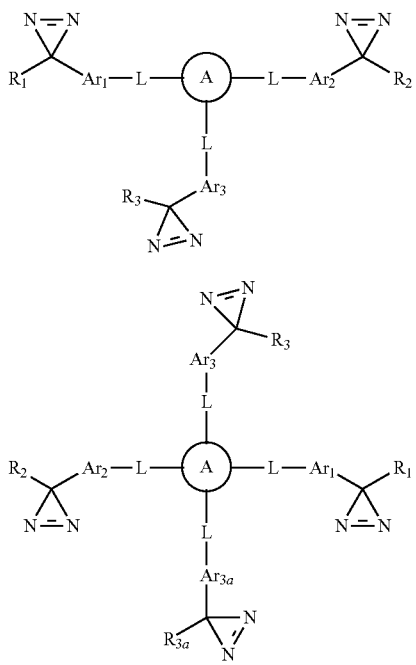

wherein,
  A is a carbon, silicon, oxygen or nitrogen central core moiety;
  L is a bond or a divalent linking or a spacer group selected from:
  —C(O)O—R$_4$—OC(O)—, —C(O)O—R$_4$—, —R$_4$—OC(O)—R$_4$—, —C(O)—R$_4$—OC(O)—, —C(O)—R$_4$—, —R$_4$—C(O)—R$_4$—, —O—R$_4$—OC(O)—, —O—R$_4$—O—, —O—R$_4$—, —R$_4$—O—R$_4$—, —C(O)NR$_5$—R$_4$—OC(O)—, —C(O)NR$_5$—R$_4$—NR$_5$C(O)—, —C(O)NR$_5$—R$_4$—, —R$_4$—NR$_5$C(O)—R$_4$—, —C(O)—R$_4$—NR$_5$C(O)—, —NR$_5$—R$_4$—OC(O)—, —NR$_5$—R$_4$—NR$_5$C(O)—, —NR$_5$—R$_4$—, —R$_4$—NR$_5$—R$_4$—, —NR$_5$—R$_4$—NR$_5$—, —R$_4$—, and

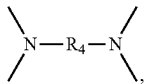

where each occurrence of R$_4$ may be the same or different which is a divalent group independently selected from (C$_1$-C$_{12}$)alkyl, (C$_3$-C$_{12}$)cycloalkyl, (C$_6$-C$_{12}$)aryl, (C$_6$-C$_{12}$)aryl(C$_1$-C$_{12}$)alkyl, (C$_6$-C$_{10}$)heteroaryl, (C$_6$-C$_{10}$)heteroaryl(C$_1$-C$_{12}$)alkyl, —(CH$_2$—CH$_2$—O)$_a$—, where a is an integer from 1 to 10, provided that when R$_4$ is —(CH$_2$—CH$_2$—O)$_a$— then the oxygen end of said group is linked only with either carbon or silicon containing linking group, which are optionally substituted with a group selected from halogen, —OH, (C$_1$-C$_4$)alkyl, (C$_1$-C$_4$)alkoxy, (C$_6$-C$_{10}$)aryl, (C$_6$-C$_{10}$)aryloxy, (C$_6$-C$_{12}$)aralkyl and (C$_6$-C$_{12}$)aralkyloxy; and R$_5$ is hydrogen, (C$_1$-C$_6$)alkyl, (C$_6$-C$_{10}$)aryl or (C$_6$-C$_{10}$)aralkyl;
  R$_1$, R$_2$, R$_3$ and R$_{3a}$ are the same or different and each is independently selected from (C$_1$-C$_{12}$)alkyl, where portions of hydrogen on alkyl are replaced with fluorine, (C$_1$-C$_{12}$)perfluoroalkyl, (C$_6$-C$_{12}$)aryl, (C$_6$-C$_{12}$)aryl(C$_1$-C$_{12}$)alkyl, where portions of hydrogen on alkyl are replaced with fluorine, and (C$_6$-C$_{12}$)arylperfluoro(C$_1$-C$_{12}$)alkyl; and
  Ar$_1$, Ar$_2$, Ar$_3$ and Ar$_{3a}$ are the same or different and each is independently selected from (C$_6$-C$_{12}$)arylene or (C$_6$-C$_{12}$)heteroarylene group optionally substituted with a group selected from halogen, —OH, (C$_1$-C$_4$)alkyl, (C$_1$-C$_4$)alkoxy, (C$_6$-C$_{10}$)aryl, (C$_6$-C$_{12}$)aryloxy, (C$_6$-C$_{12}$)aryl(C$_1$-C$_4$)alkyl and (C$_6$-C$_{12}$)aryl(C$_1$-C$_4$)alkyloxy; and
  a carrier solvent.

6. The composition of claim 5, wherein the polymer is selected from the group consisting of:
  a polycycloolefinic polymer;
  a polyacrylate;
  polyvinyl butyral;
  polyvinyl trimethylsilane (PVTMS);
  hydrogenated styrenic block copolymer;
  ethyl cellulose; and
  poly(4-tert-butyl-styrene).

7. The composition of claim 5, wherein the polymer is a polycycloolefinic polymer comprising at least one repeat unit represented by formula (IIIA), said repeat unit is derived from a monomer of formula (III):

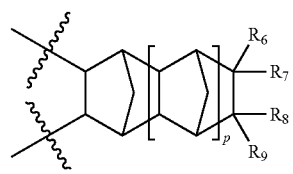

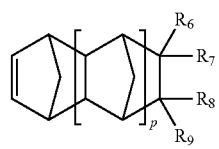

wherein:
  ⁓⁓⁓ denotes a place of bonding with another repeat unit;
  p is an integer 0, 1 or 2;
  R$_6$, R$_7$, R$_8$ and R$_9$ are the same or different and each independently of one another is selected from hydrogen, linear or branched (C$_1$-C$_{16}$)alkyl, (C$_1$-C$_{16}$)alkenyl, hydroxy(C$_1$-C$_{16}$)alkyl, perfluoro(C$_1$-C$_{12}$)alkyl, (C$_3$-C$_{12}$)cycloalkyl, (C$_6$-C$_{12}$)bicycloalkyl, (C$_7$-C$_{14}$)tricycloalkyl, (C$_6$-C$_{10}$)aryl, (C$_6$-C$_{10}$)aryl(C$_1$-C$_3$)alkyl, perfluoro(C$_6$-C$_{10}$)aryl, perfluoro(C$_6$-C$_{10}$)aryl(C$_1$-C$_3$)alkyl, di(C$_1$-C$_2$)alkylmaleimide(C$_3$-C$_6$)alkyl, di(C$_1$-C$_2$)alkylmaleimide(C$_2$-C$_6$)alkoxy(C$_1$-C$_2$)alkyl, hydroxy, (C$_1$-C$_{12}$)alkoxy, (C$_3$-C$_{12}$)cycloalkoxy, (C$_6$-C$_{12}$)bicycloalkoxy, (C$_7$-C$_{14}$)tricycloalkoxy, (C$_1$-C$_{12}$)alkoxy(C$_1$-C$_8$)alkyl, (C$_6$-C$_{10}$)aryloxy(C$_1$-C$_3$)alkyl, (C$_5$-C$_{10}$)heteroaryloxy(C$_1$-C$_3$)alkyl, (C$_6$-C$_{10}$)aryloxy, (C$_5$-C$_{10}$)heteroaryloxy, (C$_1$-C$_6$)acyloxy, (C$_1$-C$_6$)acyloxy, oxiranyl(C$_0$-C$_8$)alkyl, oxiranyl(CH$_2$)$_c$O(CH$_2$)$_d$—, halogen or a group of formula (A):

wherein:
  c is an integer 0, 1, 2, 3 or 4;
  d is an integer 0, 1, 2, 3 or 4; and
  R is linear or branched (C$_1$-C$_6$)alkyl, (C$_5$-C$_8$)cycloalkyl, (C$_6$-C$_{10}$)aryl or (C$_7$-C$_{12}$)aralkyl; where each of the aforementioned substituents are optionally substituted with a group selected from halogen or hydroxy.

8. The composition of claim 7, wherein the polymer comprises one or more repeat units derived from the corresponding monomers selected from the group consisting of:
bicyclo[2.2.1]hept-2-ene (NB);
5-butylbicyclo[2.2.1]hept-2-ene (BuNB);
5-hexylbicyclo[2.2.1]hept-2-ene (HexNB);
5-octylbicyclo[2.2.1]hept-2-ene (OctNB);
5-(but-3-en-1-yl)bicyclo[2.2.1]hept-2-ene (1-ButenylNB);
5-(but-2-en-1-yl)bicyclo[2.2.1]hept-2-ene (2-ButenylNB);
5-(but-1-en-1-yl)bicyclo[2.2.1]hept-2-ene (3-ButenylNB);
5-perfluoroethylbicyclo[2.2.1]hept-2-ene ($C_2F_5NB$);
5-n-perfluorobutylbicyclo[2.2.1]hept-2-ene ($C_4F_9NB$);
5-perfluorohexylbicyclo[2.2.1]hept-2-ene ($C_6F_{13}NB$);
norbornenyl-2-trifluoromethyl-3,3,3-trifluoropropan-2-ol (HFANB);
1-(3-(bicyclo[2.2.1]hept-5-en-2-yl)propyl)-3,4-dimethyl-1H-pyrrole-2,5-dione (PrDMMINB);
1-(4-(bicyclo[2.2.1]hept-5-en-2-yl)butyl)-3,4-dimethyl-1H-pyrrole-2,5-dione (BuDMMINB);
1-(6-(bicyclo[2.2.1]hept-5-en-2-yl)hexyl)-3,4-dimethyl-1H-pyrrole-2,5-dione (HexDMMINB);
5-phenethylbicyclo[2.2.1]hept-2-ene (PENB);
5-((2-(2-methoxyethoxy)ethoxy)methyl)bicyclo[2.2.1]hept-2-ene (NBTON);
bicyclo[2.2.1]hept-5-en-2-yl(ethoxy)dimethylsilane (NB-SiMe$_2$(OEt);
bicyclo[2.2.1]hept-5-en-2-ylmethyl acetate (MeOAcNB); and
bicyclo[2.2.1]hept-5-en-2-ylmethanol (MeOHNB).

9. The composition of claim 5, wherein the polymer is a copolymer of maleic anhydride and at least one repeat unit of formula (IIIA).

10. The composition of claim 9, wherein the maleic anhydride ring of the copolymer is at least partially opened with an alcohol.

11. The composition of claim 10, wherein the polymer is selected from the group consisting of:
a copolymer containing repeating units derived from bicyclo[2.2.1]hept-2-ene and maleic anhydride ring opened with n-butanol; and
a copolymer containing repeating units derived from 5-n-perfluorobutylbicyclo[2.2.1]hept-2-ene and maleic anhydride ring opened with n-butanol.

12. The composition of claim 7, wherein the polymer is selected from the group consisting of:
poly(5-hexylbicyclo[2.2.1]hept-2-ene) (poly(HexNB));
poly(5-(but-3-en-1-yl)bicyclo[2.2.1]hept-2-ene) (poly(1-ButenylNB));
poly(5-n-perfluorobutylbicyclo[2.2.1]hept-2-ene) (poly($C_4F_9NB$));
a copolymer of bicyclo[2.2.1]hept-2-ene (NB) and bicyclo[2.2.1]hept-5-en-2-yl(ethoxy)dimethylsilane (NB-SiMe$_2$(OEt);
a copolymer of norbornenyl-2-trifluoromethyl-3,3,3-trifluoropropan-2-ol (HFANB) and bicyclo[2.2.1]hept-5-en-2-ylmethanol (MeOHNB); and
a copolymer containing repeating units derived from bicyclo[2.2.1]hept-2-ene and maleic anhydride ring opened with n-butanol.

13. The composition of claim 5 comprising the compound of formula (IA), which is selected from the group consisting of:
methylene bis(4-(3-(trifluoromethyl)-3H-diazirin-3-yl)benzoate);
ethane-1,2-diyl bis(4-(3-(trifluoromethyl)-3H-diazirin-3-yl)benzoate);
propane-1,3-diyl bis(4-(3-(trifluoromethyl)-3H-diazirin-3-yl)benzoate);
butane-1,4-diyl bis(4-(3-(trifluoromethyl)-3H-diazirin-3-yl)benzoate);
3,3'-((oxybis(methylene))bis(4,1-phenylene))bis(3-(trifluoromethyl)-3H-diazirine);
3,3'-((oxybis(ethane-2,1-diyl))bis(4,1-phenylene))bis(3-(trifluoromethyl)-3H-diazirine);
3-(trifluoromethyl)-3-(4-(3-((4-(3-(trifluoromethyl)-3H-diazirin-3-yl)benzyl)oxy)propyl)phenyl)-3H-diazirine;
3-(trifluoromethyl)-3-(4-(2-((4-(3-(trifluoromethyl)-3H-diazirin-3-yl)benzyl)oxy)ethyl)phenyl)-3H-diazirine;
4-(3-(trifluoromethyl)-3H-diazirin-3-yl)benzyl 4-(3-(trifluoromethyl)-3H-diazirin-3-yl)benzoate;
4-(3-(trifluoromethyl)-3H-diazirin-3-yl)phenethyl 2-(4-(3-(trifluoromethyl)-3H-diazirin-3-yl)phenyl)acetate;
2-oxo-2-(4-(3-(trifluoromethyl)-3H-diazirin-3-yl)phenyl)ethyl 3-(3-(trifluoromethyl)-3H-diazirin-3-yl)benzoate;
1,3-bis(4-(3-(trifluoromethyl)-3H-diazirin-3-yl)phenyl)propan-1-one;
1,3-bis(4-(3-(trifluoromethyl)-3H-diazirin-3-yl)phenyl)propan-2-one;
(4-(3-(trifluoromethyl)-3H-diazirin-3-yl)phenoxy)methyl 3-(3-(trifluoromethyl)-3H-diazirin-3-yl)benzoate;
1,2-bis(4-(3-(trifluoromethyl)-3H-diazirin-3-yl)phenoxy)ethane;
3-(trifluoromethyl)-3-(4-(3-(4-(3-(trifluoromethyl)-3H-diazirin-3-yl)phenoxy)propyl)phenyl)-3H-diazirine;
(N-methyl-4-(3-(trifluoromethyl)-3H-diazirin-3-yl)benzamido)methyl 4-(3-(trifluoromethyl)-3H-diazirin-3-yl)benzoate; and
N,N'-methylenebis(N-methyl-4-(3-(trifluoromethyl)-3H-diazirin-3-yl)benzamide).

14. The composition of claim 5 comprising the compound of formula (II) or (IIA), which is selected from the group consisting of:
2-ethyl-2-(((4-(3-(trifluoromethyl)-3H-diazirin-3-yl)benzoyl)oxy)methyl)propane-1,3-diyl bis(4-(3-(trifluoromethyl)-3H-diazirin-3-yl)benzoate);
2-(perfluoroethyl)-2-(((4-(3-(trifluoromethyl)-3H-diazirin-3-yl)benzoyl)oxy)methyl)propane-1,3-diyl bis(4-(3-(trifluoromethyl)-3H-diazirin-3-yl)benzoate);
3,3'-((((2-ethyl-2-(((4-(3-(trifluoromethyl)-3H-diazirin-3-yl)benzyl)oxy)methyl)propane-1,3-diyl)bis(oxy))bis(methylene))bis(4,1-phenylene))bis(3-(trifluoromethyl)-3H-diazirine); and
3,3'-((((2-(perfluoroethyl)-2-(((4-(3-(trifluoromethyl)-3H-diazirin-3-yl)benzyl)oxy)methyl)propane-1,3-diyl)bis(oxy))bis(methylene))bis(4,1-phenylene))bis(3-(trifluoromethyl)-3H-diazirine).

15. The composition of claim 5 wherein said carrier solvent is selected from the group consisting of: ethanol, isopropanol, acetone, cyclohexanone, cyclopentanone, decane, toluene, p-menthane, benzyl acetate, diethylene glycol dimethyl ether, propylene glycol monomethyl ether (PGME), propylene glycol monomethyl ether acetate (PGMEA), N-methyl-2-pyrrolidone (NMP), gamma-butyrolactone (GBL), N,N-dimethylacetamide, N,N-dimethylformamide, anisole, methyl 3-methoxypropionate, tetrahydrofuran (THF), 3-ethoxy-1,1,1,2,3,4,4,5,5,6,6,6-dodecafluoro-2-(trifluoromethyl)hexane (HFE-7500), 1,1,1,2,2,3,3,4,4-nonafluoro-4-methoxybutane, 1,1,1,2,2,3,3,4,4-nonafluoro-3-methoxybutane and mixtures in any combination thereof.

16. A cured product obtained by curing the composition of claim 5.

17. An optoelectronic or microelectronic device comprising the cured product of claim 16.

* * * * *